(12) United States Patent
Venkatraman et al.

(10) Patent No.: US 11,363,952 B2
(45) Date of Patent: Jun. 21, 2022

(54) METHODS AND SYSTEMS FOR REMOTE HEALTH MONITORING

(71) Applicant: Eko Devices, Inc., Oakland, CA (US)

(72) Inventors: Subramaniam Venkatraman, Lafayette, CA (US); Michael Thompson, San Francisco, CA (US); Scott Suarez, San Francisco, CA (US); Connor Landgraf, Albany, CA (US)

(73) Assignee: Eko Devices, Inc., Oakland, CA (US)

( * ) Notice: Subject to any disclaimer, the term of this patent is extended or adjusted under 35 U.S.C. 154(b) by 0 days.

(21) Appl. No.: 16/997,464

(22) Filed: Aug. 19, 2020

(65) Prior Publication Data

US 2022/0054008 A1 Feb. 24, 2022

(51) Int. Cl.
G08B 1/08 (2006.01)
A61B 5/00 (2006.01)
G16H 40/67 (2018.01)
G06F 21/31 (2013.01)

(52) U.S. Cl.
CPC .......... *A61B 5/0004* (2013.01); *A61B 5/0024* (2013.01); *A61B 5/7264* (2013.01); *A61B 5/742* (2013.01); *G06F 21/31* (2013.01); *G16H 40/67* (2018.01)

(58) Field of Classification Search
CPC ... A61B 5/0004; A61B 5/7264; A61B 5/0024; A61B 5/742; G16H 40/67; G06F 21/31
See application file for complete search history.

(56) References Cited

U.S. PATENT DOCUMENTS

| 9,736,625 | B1 | 8/2017 | Landgraf et al. | |
| 10,806,404 | B2* | 10/2020 | Soto | G16H 50/50 |
| 2005/0144042 | A1* | 6/2005 | Joffe | G16H 10/20 705/2 |
| 2009/0177495 | A1* | 7/2009 | Abousy | G16H 50/20 705/3 |
| 2016/0287207 | A1* | 10/2016 | Xue | A61B 5/743 |
| 2017/0296107 | A1* | 10/2017 | Reid | A61B 5/002 |

FOREIGN PATENT DOCUMENTS

WO 2020041363 A1 2/2020

* cited by examiner

*Primary Examiner* — Toan N Pham
(74) *Attorney, Agent, or Firm* — McCoy Russell LLP

(57) ABSTRACT

Methods and systems are provided for real-time biological sensor data transmission and analysis. In one example, a method includes obtaining biological sensor data of a patient from one or more sensors of a health monitoring device and transmitting the biological sensor data in real-time from a patient's transmitting device to a clinician's remote receiving device that is wirelessly communicating with the transmitting device. Further, at the transmitting device, responsive to a request for analysis and/or storage from the remote receiving device, transmitting the real-time biological sensor data stream or a recording of the real-time biological sensor data to a computing sever for analysis and/or storage.

23 Claims, 10 Drawing Sheets

METHODS AND SYSTEMS FOR REMOTE HEALTH MONITORING

FIELD

The present disclosure relates to medical devices utilizing wireless electronic communications. More specifically, this disclosure relates to methods and systems for sending, receiving, analyzing, and interpreting data from wireless sensors over a network.

BACKGROUND

Remote monitoring devices have been shown to be an inexpensive and effective solution to providing patient care when in-person consultations are impossible or unfeasible. Examples of remote monitoring devices include digital stethoscopes, heart rate monitors, handheld echocardiography (HHE) or portable cardiac ultrasound devices, and other similar devices capable of recording time-varying patient data, as well as devices that capture instantaneous data such as glucose monitoring devices, blood pressure monitors, pulse oximeters, and so on. Remote monitoring may involve acquiring patient data via a monitoring device, and transmitting the patient data to a remote caregiver via a transmitting device. In some cases, a patient's smart phone or similar device connected to the Internet may be used as a transmitting device. For example, a patient may use a digital stethoscope to record a sample of their heart sounds, which are subsequently transmitted wirelessly to an app on the patient's phone, which then transmits the recording over the Internet to a specialist caregiver. The transmission of patient data may be live streamed to a remote care provider, or the patient data may be transmitted asynchronously (e.g., via an email, or uploaded to a folder in a hospital network to be viewed later).

However, there are potential issues with streaming patient data. As one example, regular, periodic, and/or long term monitoring also increases the risks of unauthorized access to private patient data, and current remote monitoring systems may not offer sufficient protection in the collection of robust data and/or integration with existing hospital systems, including EMRs.

BRIEF DESCRIPTION

In one embodiment, a method for streaming acquired data from one or more medical devices, comprises: transmitting, in real-time or near real-time, the acquired data, via a transmitting computing device wirelessly coupled to the one or more medical devices, to a receiving computing device; rendering, in real-time or near real-time the acquired data via a first application executing at the transmitting device; rendering, in real-time or near real-time, the transmitted data via a second application executing at the receiving device; and responsive to one or more signals from the receiving device, performing one or more corresponding actions on the acquired biological data; wherein the one or more actions include processing the acquired data using a trained artificial intelligence algorithm.

In this way, an artificial intelligence enabled telehealth platform may be provided that empowers a remote clinician (via the receiving device) to perform artificial intelligence analysis on live streaming data. For example, real-time data such as biological sensor data acquired from one or more monitoring devices may be streamed from a patient at one physical location to a healthcare provider at another physical location via a computing device (such as a computer, smart phone, or tablet) in a way that is efficient, secure, and that integrates effectively with existing healthcare systems (hospital networks, EMR's, etc.). Further, by enabling the receiving device to initiate desired actions on the real time data, real-time clinician assistance may be provided, which improves diagnostic efficiency and patient outcomes.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
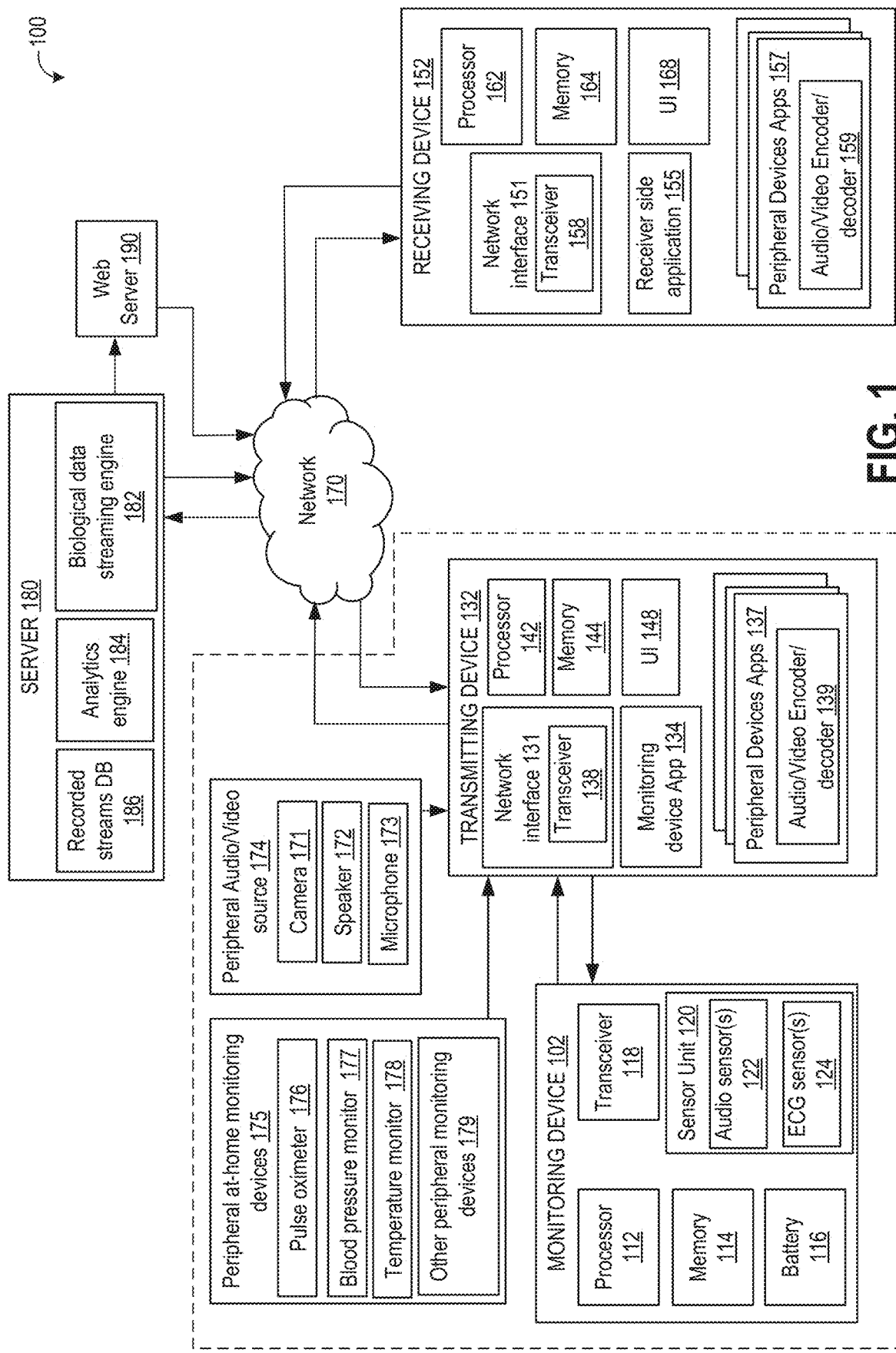
FIG. 1 shows a block diagram of a telehealth system according to an exemplary embodiment of the disclosure.

Telehealth systems enable clinicians to remotely monitor patients. Current telehealth systems rely on information acquired and communicated to a remote clinician by a patient to enable monitoring and diagnosis of various health conditions. The information provided by the patient may include data acquired from a telehealth monitoring device, such as a digital stethoscope. However, current telehealth systems have various shortcomings. As one example, as patient health data is transmitted from an authenticated source (that is, the patient) through a communication network (e.g., internet) to a remote device, patient health data vulnerable to unauthorized access.

Further, during a remote telehealth session, the remote clinician may require assistance in interpreting the health data received from the patient and/or may need to verify their own diagnosis. Current systems do not provide remote clinician assistance, such as diagnosis verification, while protecting patient health information. Furthermore, current systems do not support a remote clinician in real-time. As a result, diagnosis is often delayed, which in turn causes delay in treatment. For example, during telehealth sessions, as clinicians rely on data (e.g., biological sensor data) sent by the patients for evaluation, clinician confidence in the data received may be impacted. Further, as clinicians lack support for reliable and immediate assessment (e.g., during a single telehealth session) of data received from the patients, there is uncertainty in diagnosis. Consequently, a patient may be forced to go to a healthcare facility after a telehealth session for diagnosis confirmation and/or multiple telehealth sessions are required before a reliable and confirmed diagnosis is provided.

Further still, current telehealth systems lack adaptability to increasing demand, and lack clinician and patient support for a wide-range of care, such as during epidemic and pandemic conditions, when direct contact increases the risk of transmission from patients to clinicians, and to other patients.

Thus, according to embodiments disclosed herein, the above drawbacks of telehealth systems may be at least partially addressed by a method for streaming acquired data from one or more medical devices, comprising: transmitting, in real-time or near real-time, the acquired data, via a transmitting computing device wirelessly coupled to the one or more medical devices, to a receiving computing device; rendering, in real-time or near real-time, the transmitted data at the receiving device; and responsive to one or more signals from the receiving device, performing one or more corresponding actions on the acquired biological data; wherein the one or more actions include processing the acquired data using a trained artificial intelligence algorithm.

In this way, a remote clinician, via the receiving device, may request artificial intelligence (AI) analysis on real-time or near real-time biological sensor data received from a patient during a remote telehealth session. By enabling the remote clinician to request AI analysis and providing AI analysis of patient health condition in response to the request, real-time clinician assistance is provided. The clinician may utilize the AI analysis to support their findings, which increases clinician confidence in diagnosis as well as clinician confidence in data received from the patient. Further, as the analysis may be performed in real-time or near real-time, diagnostic efficiency is improved.

By providing AI analysis for telehealth, reliable, secure, and real-time assessment may be delivered to the patients, thereby enabling the clinicians to evaluate and treat patients remotely with high fidelity.

As an example, the telehealth systems disclosed herein allows for real-time biological sensor data streams, including time-varying data such as ECG and/or auscultation data, to be processed by artificial intelligence and/or other analytics software running on a secure server. For example, concurrently with the transmission of biological sensor data streams from a monitoring device to a transmitting device and then to a receiving device, a recording of biological sensor data or the biological sensor data stream acquired via the monitoring device may be transmitted to a server, where one or more AI routines may process the recording or the data stream in order to output health condition information that may be transmitted to one or more of the transmitting device and the receiving device upon the completion of processing to the patient, the caregiver, and/or both. As discussed in further detail below, the information outputted may include diagnostics, recommendations for follow-up tests, suggestions for treatment, warning signs or cautionary information, or other similar information.

As the process of requesting and providing a patient's private medical data entails protecting patients from risks of unauthorized access in accordance with confidentiality policies and laws, systems and methods provided herein establish a secure framework for transmitting data to and from a secure server, and to a remote device. For example, patient data may not be streamed directly to a recipient, but rather to a temporary secure site that a caregiver may access via an authentication process that may include both logging into account with authorized credentials and explicitly requesting permission from the patient.

Figure 8A:
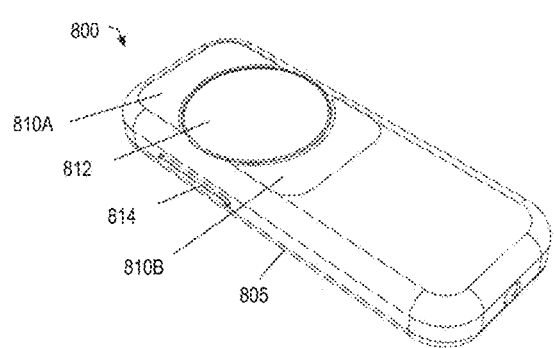
FIGS. 8A and 8B are perspective views of a monitoring device, in accordance with some embodiments.
Figure 8B:
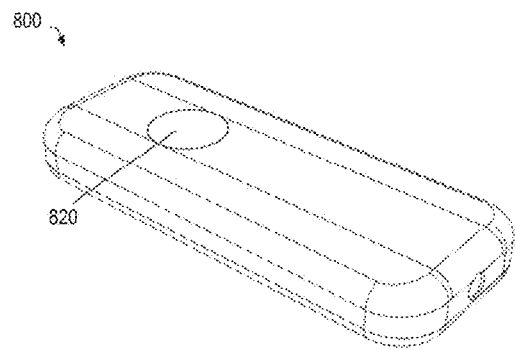
Figure 9:
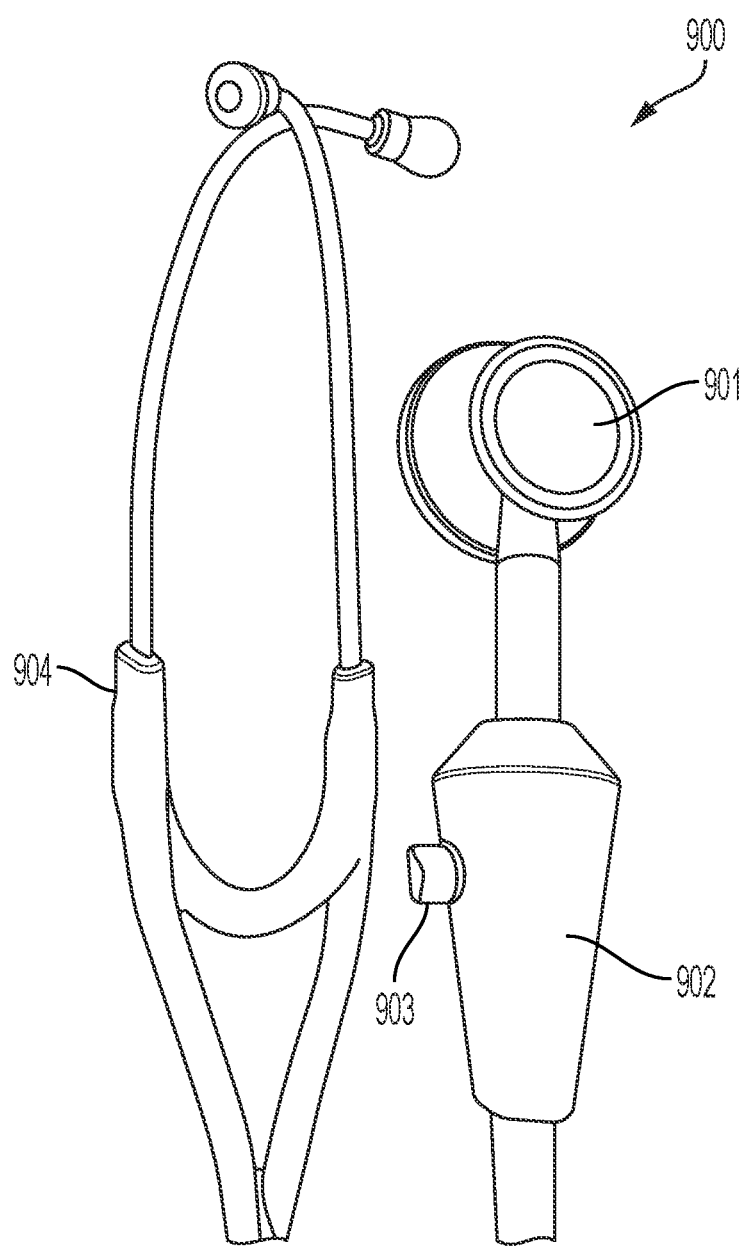
FIG. 9 is a perspective view of a stethoscope.

The following description relates to systems and methods for the management, transmission, and processing of medical data between a patient and a caregiver within a telehealth system, such as telehealth system 100 shown by FIG. 1, whereby patients may capture biological sensor data via one or more remote monitoring devices and transmit the data to a healthcare provider at a different physical location. Biological sensor data may be transmitted from a transmitting device to a remote receiving device over a communication network, either through a server as shown in telehealth system 100 of FIG. 1, or via a peer-to-peer framework such as the peer-to-peer telehealth system 200 shown in FIG. 2A. Establishment of peer-to-peer connection, including authentication, is described with respect to FIG. 2B. Transmission of real-time biological sensor data may be initiated by the transmitting device, according to the method described at FIG. 3. The biological sensor data may be acquired by multiple sensors, which may be located on a single device or on multiple devices. An example, multi-sensor monitoring device for obtaining auscultation sound data and ECG data is shown in FIGS. 8A and 8B. Another example monitoring device is a digital stethoscope for performing auscultation and is shown in FIG. 9. The transmitting device may process authentication requests according to the method described at FIG. 4 for data communication through the central server-client based telehealth system shown at FIG. 1. Further, the server may authenticate the receiving device, according to the method described at FIG. 6, in the central server-client based telehealth network of FIG. 1. The transmitting device may process one or more requests (e.g., for AI analysis, recording, integration with the EMR, etc.,) from one or more of the receiving device and/or the transmitting device during a live stream telehealth session, according to the method described at FIG. 5. During the live stream telehealth session, while transmitting the biologicals sensor data in real-time to the receiving device, the transmitting device may generate a recording of the real-time biological sensor data responsive to a storage and/or AI analysis request, and transmit the recorded data to the central server for storage and/or AI analysis. The handling of the recording (received from the transmitting device) by the central server is based on the type of request and may be performed according to the method described at FIG. 7. Further, the systems and methods described herein enable real-time audio and/or video interaction between a patient and a remote clinician through patient audio and/or video integration in the telehealth systems of FIGS. 1 and 2A, as described further below.

For the purposes of this disclosure, biological sensor data comprises any data from a patient's body that is captured using a sensor, including time-varying data such as ECG data (including multi-lead ECG data), heart sounds, lung sounds, bowel sounds, or sounds from other organs, data obtained from a pulse oximeter such as photoplethysmogram (PPG) data, etc. Biological sensor data also includes instantaneous data such as blood pressure, pulse, weight, images of the inner ear taken via an otoscope, etc. The examples of biological sensor data included herein are listed for illustrative purposes, and other types of biological sensor data may be included without departing from the scope of this disclosure.

As used herein, real-time may include the data being sent as soon as the data is collected, immediately and without an intentional delay. In this way, as soon as biological sensor is available at the transmitting device, the biological sensor data is sent to the central server in a central server/client based communication network, or in a peer-to-peer network, to the receiving device. In some instances, real-time or near real-time may refer to simultaneous or substantially simultaneous processing, such as filtering, encryption or decryption, compression, encoding, digitalization, or any other processing that may be carried out prior to, during, or after the transmission of patient data within the scope of the above definition of real-time. As used herein, near real-time may refer to the data being sent with a slight delay for example due to data filtering, encryption or decryption, compression, encoding, digitalization, and/or other data processing actions. However, the near-real time transmission of the data may still be rapid relative to when the data was made available.

Figure 2A:
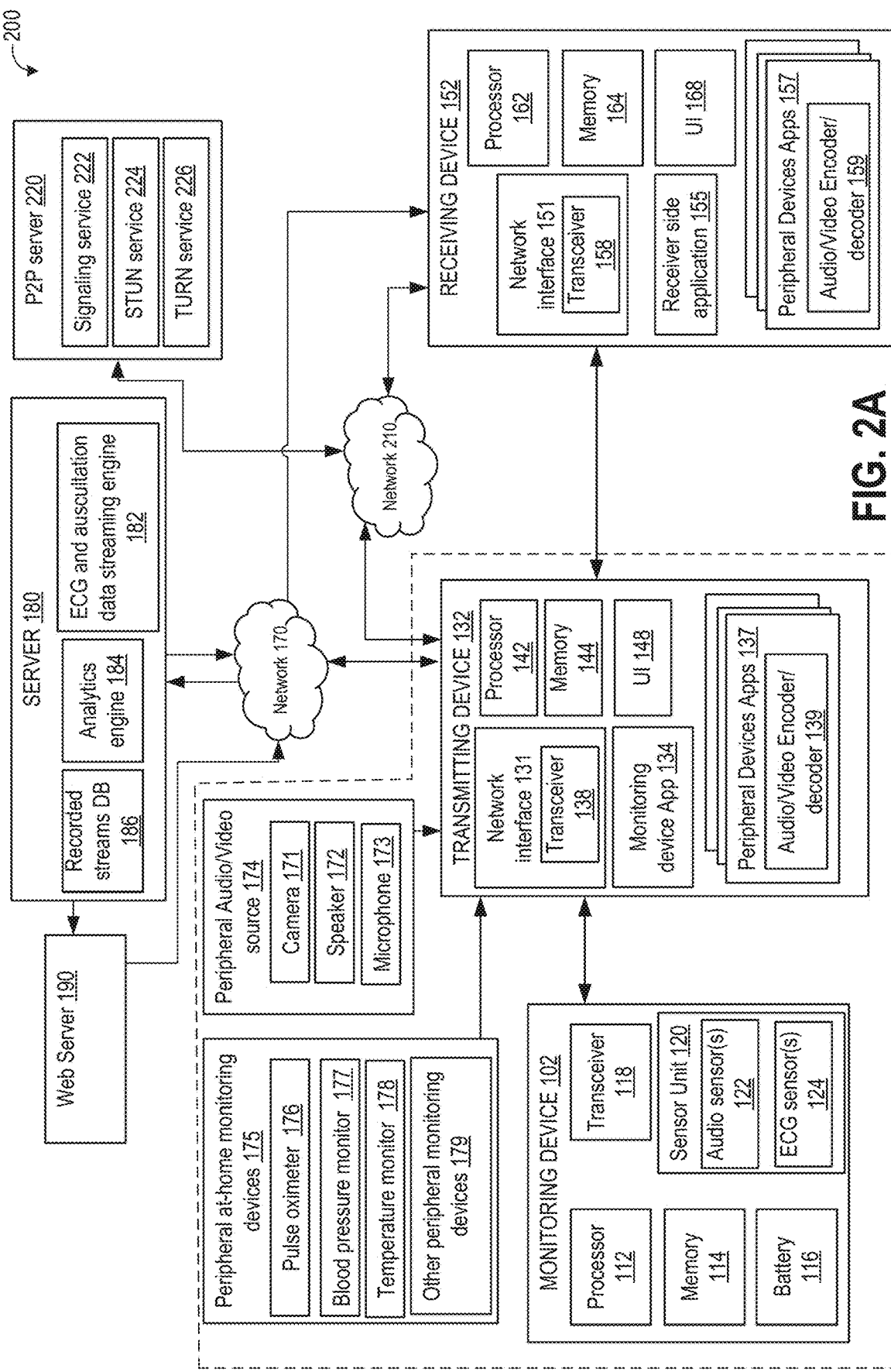
FIG. 2A shows a block diagram of a telehealth system that uses peer-to-peer technologies.
Figure 2B:
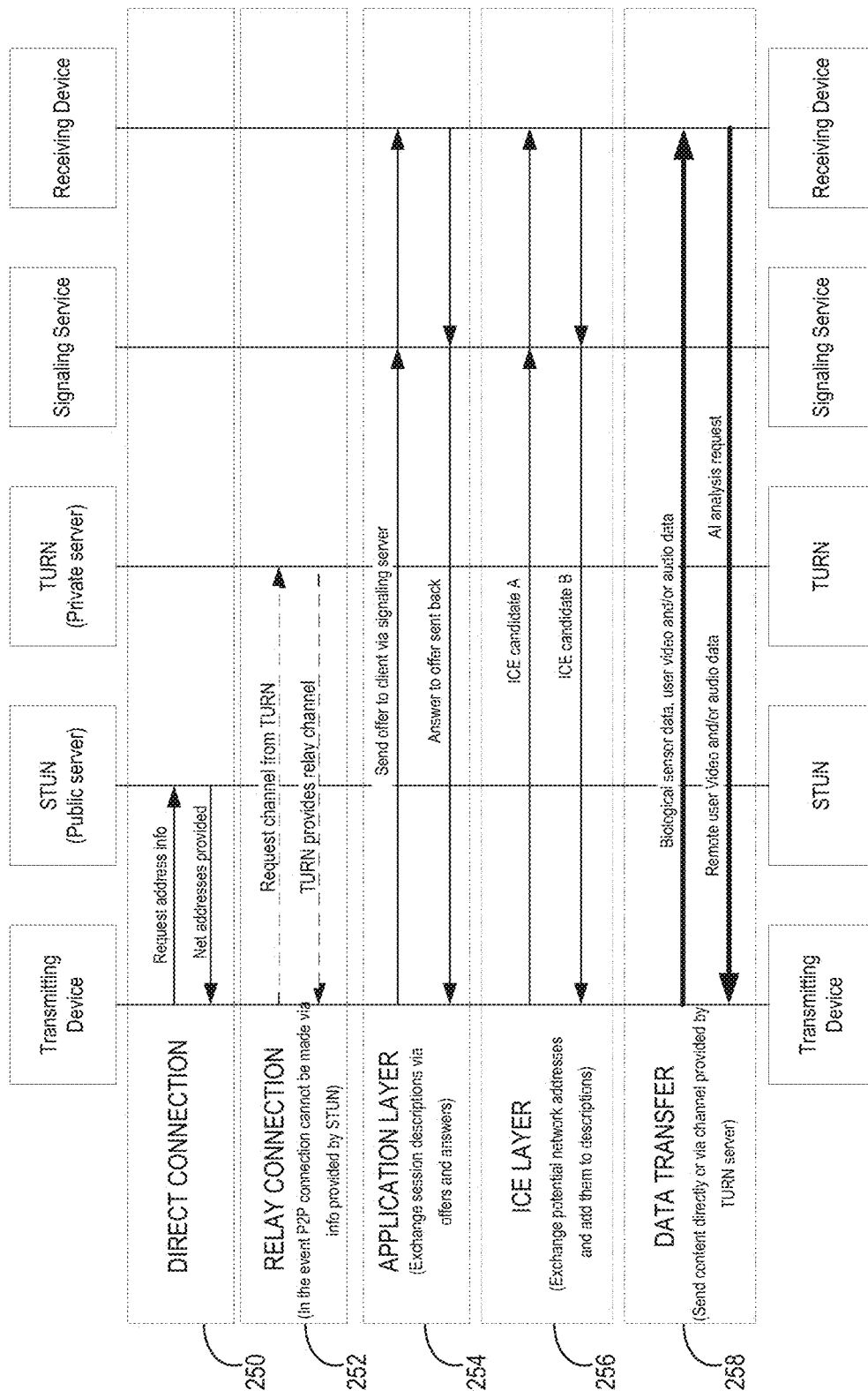
FIG. 2B shows an example timing diagram for establishing peer-to-peer connection between a transmitting device and a receiving device of a telehealth system.

Referring now to FIG. 1, an example telehealth system 100 is shown that allows a clinician to view patient data from one or more patients at remote locations. The patient may be an individual who is symptomatic with respect to a disease or condition, or an individual who is healthy and/or asymptomatic, or an individual who may be suspected of having a disease or condition or a predisposition to a disease or condition. As referenced herein, patient data refers specifically to biological sensor data; however, other types of patient data may be included without departing from the scope of this disclosure. The telehealth system 100 may be implemented to live stream biological sensor data (in real-time or near real-time) acquired from a patient by one or more monitoring devices, and transmitted to a remote clinician as discussed below. The live streaming in real-time or near real-time may be performed via an example central server and client based communications network architecture as shown in FIG. 1 or via an example peer-to-peer communications network architecture as shown in FIGS. 2A and 2B.

Referring to FIG. 1, telehealth system 100 may include a transmitting device 132, a receiving device 152, and a server 180, whereby patient data is transmitted over a network 170 from the transmitting device 132 to the receiving device 152 via the server 180. The transmitting device 132 and the receiving device 152 may be at different locations, or the transmitting device 132 at the receiving device 152 may both be at the same general location, but separated by distance or physical barriers such as walls, screens, etc. For example, the transmitting device 132 may be used from the patient's home and the receiving device 152 may be located at a hospital facility, or the transmitting device 132 may be used in a rural clinic to communicate with a clinician on the receiving device 152 at a regional hospital. Alternatively, the transmitting device 132 and the receiving device 152 may both be located within a hospital facility, where a patient uses the transmitting device 132 in a waiting room or consultation room, and a clinician receives patient data on the receiving device 152 in an office, research unit, laboratory, etc. Further, under quarantine conditions such as the conditions presented with respect to COVID19, the transmitting device 132 may be used by an attending physician in a treatment area under quarantine such as an intensive care unit (ICU) to send patient data to a specialist located outside of the quarantine area, for example, behind a screen, in a neighboring room, in another area of the facility, etc. In some embodiments, peer-to-peer (P2P) technologies may be used to transmit data directly from the transmitting device 132 to the receiving device 152 without using the server 180, as described below in reference to FIGS. 2A, 2B, and 3.

The transmitting device 132 may include a processor 142, a memory 144, a user interface (UI) 148, and a network interface 131, which may include a transceiver 138, as well as a display (e.g., screen or monitor) and/or other subsystems. The transmitting device 132 may be in the form of a desktop computing device, a laptop computing device, a tablet, a smart phone, or any other device configured to transmit data over a network. For example, a patient receiving remote care from their home may use an iPhone or iPad as the transmitting device 132.

The devices comprised by the telehealth system 100 may be communicatively connected to at least one network 170, which may include in a non-limiting manner, a wide area network (WAN); a local area network (LAN); the Internet; a wired or wireless (e.g. optical, Bluetooth, Bluetooth Low Energy (BLE), radio frequency (RF) network; a cloud-based computer infrastructure of computers, routers, servers, gateways, etc.; or any combination thereof associated therewith that allows one or more computing devices within the telehealth system 100 to connect with each other. The network 170 may be a public network, or a private network associated with a portion of a care facility, for example a surgery unit or department of a hospital, or may be more broadly located across medical devices of an entire hospital or hospital system. Each transmitting device 132 may be adapted to send and receive encrypted data over the network 170 via the network interface 131 and the transceiver 138.

The transmitting device 132 may be communicatively connected to a monitoring device 102. The monitoring device 102 may be a specially designed device for sensing a certain type or types of patient data via placement on a patient's body, and communicating the patient data to a transmitting device such as the transmitting device 132. The monitoring device 102 may include a processor 112, transceiver 118, memory 114, and battery 116. Example monitoring devices are described below in relation to FIGS. 8A, 8B, and 9. The monitoring device 102 may further include a plurality of sensors of different types or the same type. In one example, as shown in FIG. 1, the monitoring device 102 may include a sensor unit 120 having one or more audio sensors 122 and one or more electrocardiogram (ECG) sensors 124. The monitoring device 102 may include one or more other type of sensors (not shown) for obtaining physiological data from a patient in addition to the audio sensors 122 and ECG sensors 124. The one or more other type of sensors may include but not limited to 3 lead ECG sensor, pulse oximetry sensor, blood pressure sensor, temperature sensor, and imaging sensors (e.g., otoscope). Thus, the monitoring device 102 may include a combination of one or more audio sensors 122 and one or more ECG sensors 124, or a combination of audio sensors 122 and ECG sensors 124 and any other kind of sensor. When not included in the monitoring device 102, the said one or more other type of sensors may be implemented via one or more peripheral monitoring devices 175, and the telehealth system 100 may receive, transmit, and process data obtained from the monitoring device as well as the one or more peripheral monitoring devices 175, as further discussed below.

The data acquired by the monitoring device 102 via the sensor unit may include physiological data of a subject (e.g., patient) measured by the sensor unit. The physiological data is alternatively referred to herein as biological sensor data or simply biological data. The biological data may include auscultation data comprising one or more of heart sound data, lung sound data and bowel sound data, ECG data, and/or any other type of data that may be acquired from a sensor capable of acquiring patient physiological data in real-time. Thus, the biological sensor data sensed by the monitoring device correlates to the type of sensors in the monitoring device 102 and may include PPG data, blood pressure data, SpO2 data, otoscope data, and temperature data. It will be appreciated that the types of sensors listed above are mentioned for illustrative purposes, and the monitoring device 102 may additionally include other types of sensors for obtaining physiological data of a patient without departing from the scope of this disclosure.

The biological data from the plurality of sensors of the sensor unit 120 of the monitoring device 102 may be acquired simultaneously or selectively from one or more selected subset of sensors of the plurality of sensors. Said another way, while the plurality of sensors are present, a user may select, via the monitoring device 102 or via the transmitting device 132 communicatively coupled to the monitoring device 102, one or more subset of sensors from which corresponding data may be selectively acquired. In some embodiments, wherein the sensor unit 120 includes audio sensors 122 and ECG sensors 124, both the auscultation and ECG data may be acquired simultaneously or selectively independent of each other. For example, the monitoring device 102 may acquire auscultation data (e.g., via a digital stethoscope) but no ECG data, or ECG data but no auscultation data. Thus, while audio and ECG sensors may both be present, auscultation or ECG data may be selectively obtained.

The monitoring device 102 may communicate biological sensor data acquired by the sensor unit 120 data (e.g., auscultation data, ECG data, and other sensor data) wirelessly (e.g., via BLE) to the transmitting device 132 capable of transmitting the data over a network to the receiving device. In some embodiments, the biological sensor data may be encrypted, compressed, filtered, and/or otherwise processed by the monitoring device 102 prior to transmission to the transmitting device 132.

The monitoring device 102 and the transmitting device 132 may be communicatively coupled via a wireless personal area network (PAN) technology such as BLE. In other embodiments, any PAN technology may be used, such as induction wireless, infrared wireless, ultra wideband (UWB), or any other similar technology for wireless communication between co-located devices.

Telehealth system 100 may also include one or more peripheral at-home monitoring devices 175, which may be used to supplement the patient data received by the transmitting device 132 from the monitoring device 102. For example, in addition to auscultation, ECG, and/or other time varying biological sensor data acquired by the monitoring device 102, the transmitting device 132 may receive readings from a pulse oximeter 176, a blood pressure monitor 177, a temperature monitor 178, and/or one or more other peripheral monitoring devices 179. Additionally, in order to facilitate communication between a user of the monitoring device 102 and a remote user (e.g., clinician) monitoring data from the monitoring device, the telehealth system 100 may include via the transmitting device 132, one or more peripheral audio and video sources 174, such as a camera 171, a speaker 172, and/or a microphone 173. For example, a patient may use one of the peripheral audio and video sources 174 that are communicatively coupled to the transmitting device 132 to record a message (e.g., audio message, video message, or a combination thereof) via one or more of the camera 171 and the speaker 172 that may be transmitted to a clinician via the transmitting device 132.

In some embodiments, one or more of patient audio and video data obtained from the one or more audio and/or video sources may be streamed in real-time or near real-time to the transmitting device 132, and subsequently to a receiving device 152 (also referred to herein as receiver device or simply receiver). In particular, the one or more of patient and video data obtained from the one or more audio and/or video sources may be transmitted, via the transmitting device, in real-time or near real-time in parallel with biological sensor data obtained from the monitoring device.

The transmitting device 132 may have a monitoring device application 134 installed on it to facilitate, protect, and/or streamline communication with the monitoring device 102. The monitoring device application 134 (also referred to herein as monitoring device app) may be a mobile, computer, or web application (e.g., browser). For example, the monitoring device app 134 may be configured to reduce any latency or performance issues that may arise when sending data, and/or to ensure that any biological sensor data sent to the receiving device 152 is encrypted to prevent any unauthorized access. For example, at the transmitting device 132, the biological sensor data received from the monitoring device 102 may be filtered (e.g., to removed unwanted data such as background noise, people talking, etc.) and compressed, in addition to encryption, in order to refine the relevant signals and/or facilitate rapid and efficient transmission while ensuring time synchronization among the various data obtained from the various sensors (e.g., time synchronization between heart sound data and ECG data).

Similarly, biological sensor data acquired by the monitoring device 102 may be pre-processed prior to transmission to the transmitting device 132. As a non-limiting example, the monitoring device 102 may obtain audio data from the audio sensor 122 and apply an analog-to-digital converter to generate a digital audio data stream. One or more digital filters (e.g., low pass filter) may be applied to digitized audio data stream in order to reduce artifacts and distortion during a subsequent compression process via an encoder, such as adaptive differential pulse-code modulation (ADPCM) encoder. Electrical signals from the ECG sensors 124 may be digitized, filtered, and compressed in a manner similar to the audio data processing discussed above. The filtered and compressed audio and ECG sensor data received at the transmitting device 132 may be decoded and further pre-processed at the transmitting device for live streaming in real-time or near real-time to the receiving device. Simultaneously, the audio and ECG sensor data may be rendered via a display portion of user interface 148 and a sound rendering device (e.g., ear phone, speaker, etc.) coupled to the transmitting device. The pre-processing at the transmitting device may include additional filtering and compression prior to transmitting the sensor data stream. For example, prior to transmission from the transmitting device 132, the sensor data may be filtered, encoded by an encoding scheme such as JavaScript Object Notation (JSON), and compressed. Other encoding schemes for live streaming biological sensor data are also within the scope of the disclosure.

The transmitting device 132 may include one or more installed peripheral device apps 137. The one or more peripheral device apps 137 may include an audio/video encoder/decoder 139, in order to process and transmit any audio or video data received. For example, one of the other peripheral monitoring devices 179 or the transmitting device 132 may use the camera 171 and the microphone 173 to generate and/or record a video, which may be processed by the audio/video encoder 139 in order to be transmitted to the receiving device 152 via the transmitting device 132. In some embodiments, biological data obtained and transmitted from the monitoring device 102, the patient video and/or audio data (from peripheral audio and/or video source 174), and the other biological sensor data from the peripheral at-home monitoring devices 175 may be processed and/or streamed by the monitoring device app 134. In other embodiments, the patient video and/or audio data (from peripheral audio and/or video source 174) may be processed and/or streamed separately via a $3^{rd}$-party service (e.g., Twilio, Zoom, Sykpe, etc.)

Similar to the transmitting device 132, the receiving device 152 may include a processor 162, a memory 164, a UI 168, and a network interface 151 that may include a transceiver 158, as well as a display (e.g., screen or monitor) and/or other subsystems. The receiving device 152 may be in the form of a desktop computing device, a laptop computing device, a tablet, a smart phone, or any other device configured to transmit data over network 170. In order to process data acquired by the monitoring device 102, the peripheral at-home monitoring devices 175, and/or the peripheral audio/video sources 174, the receiving device 152 may include device receiver side application 155 (also referred to as receiver side app) and one or more peripheral device apps 157, including an audio/video encoder/decoder 159 for processing any audio or visual data sent over network 170. For example, the audio/video encoder/decoder 159 may be used to decode and render a video stream sent to a clinician by a patient via one of the other peripheral monitoring devices 179 that makes use of the camera 171 and the microphone 173.

The processors referred to herein, including the transmitting device processor 142, receiving device processor 162, and the monitoring device processor 112, may be any suitable processor, processing unit, or microprocessor, for example, and may be integrally constructed as part of a programmable device such as a smart phone or tablet. In some embodiments, the processor may be a multi-processor system, and may include one or more additional processors that are identical or similar to each other and that are communicatively coupled via an interconnection bus.

The computer memories referred to herein, including those found in the transmitting device memory 144, the receiving device memory 164, and the monitoring device memory 114, include a tangible and non-transitory computer readable medium in which programming instructions are stored, and may include one or more data storage structures, such as optical memory devices, magnetic memory devices, or solid-state memory devices, for storing programs and routines executed by the processor(s) to carry out various functionalities disclosed herein. The memories 144, 164, and 114 may include volatile and/or non-volatile or removable and non-removable media for storage of electronic-formatted information such as computer readable program instructions or modules of computer readable program instructions, data, etc. that may be stand-alone or as part of a computing device. Examples of computer memory may include, but are not limited to RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor.

The server 180 in the telehealth system 100 may include biological data streaming engine 182 for transmitting biological sensor data from the transmitting device 132 to the receiving device 152 over the network 170 in real time. The biological sensor data streaming engine may be responsible for various processes involved in receiving, buffering, temporarily storing, encrypting, manipulating, or otherwise processing time series data received from the monitoring device 102 via the transmitting device 132. The role of the server 180 in the live streaming of patient data in telehealth system 100 is described in further detail below with respect to FIG. 4.

The server 180 may have the capacity to store recorded time series data streamed from a patient via the transmitting device 132 in a recorded stream database 186. In one example, as heart conditions often develop over long periods of time and may improve or worsen gradually, a component of patient care may involve identifying and monitoring patterns in patient data over months or years. To facilitate the identification of trends and/or anomalies that emerge over longer time frames, the server 180 may collect, store, and periodically compare a plurality of samples of patient data taken at different times. The server 180 may collect samples in the form of any kind of data, including recorded images from camera 171, audio streams from audio sensor 122 of the monitoring device 102, video streams from one or more other peripheral monitoring devices 179, which may be encoded by audio/video encoder 139, time series data from sensors such as ECG sensors 124, as well as readings of pulse, blood pressure, temperature, etc. In order to process this information, the server 180 may also include an analytics engine 184, which may run one or more artificial intelligence (AI) programs to analyze the various types of patient data streamed by the transmitting device 132. For example, analytics engine 184 may compare ECG data generated by ECG sensors 124 at consultations held every month for a period of a year, in order to determine whether an arrhythmia is stable or getting worse, or whether a patient's heart disease is evolving in response to a treatment.

Analytics engine 184 may use one or more artificial intelligence based algorithms, including trained algorithms such as machine learning algorithms based on neural networks or other similar technologies, to identify new patterns in time series data. For example, a trained artificial intelligence (AI) algorithm may be a trained machine learning algorithm that may be implemented by a deep learning approach.

The trained artificial intelligence algorithm may take as input recorded biological sensor data in order to determine a health condition of a patient, and in some examples, determine a specific treatment. For example, the biological sensor data may be input into the trained AI algorithm. Additional information such as age, gender, recording position, weight, or organ type may be inputted into the trained AI algorithm. The trained AI algorithm may output a likelihood of a pathology or disease, a disease severity score, or a healthy state, for example. In some cases, the trained AI algorithm may be used to analyze a subset of biological sensor data, such as audio data, ECG data, or both the audio and the ECG data.

As a non-limiting example, a trained AI algorithm may take as input time-synchronized time series data that includes ECG data and heart sound data, obtained from an ECG transducer and audio transducer of the monitoring device, process the input ECG and heart sound data, and output a heart condition of the patient. During the processing, the AI algorithm may extract features of the input ECG and heart sound data, and evaluate the extracted features with respect to plurality of annotated data sets comprising time synchronized ECG data and heart sound data, wherein the plurality of annotated data sets (labelled by domain experts) are stored in a database of the analytics engine, the plurality of annotated data sets obtained from a plurality of subjects. For example, the features of the audio data, the ECG data, or a combination of the audio and ECG data can be used to determine a heart condition of a subject. In some examples, the trained AI algorithm may compare and identify a number of examples from the annotated data sets that are closest in terms of a plurality of features of ECG data and/or audio data to a recorded ECG or audio data. The identified datasets that include features highly similar to the recorded data that is currently analyzed may be provided as output to assist the clinician in diagnosis.

Additionally, the trained artificial intelligence algorithm may analyze the input ECG and heart sound data with a plurality of ECG and hear sound data of the same patient obtained at various times prior to the input data to determine progression of the heart condition. The role of the server 180 in handling recording and AI requests is discussed in further detail below in relation to FIG. 7.

The trained AI algorithm may be implemented by a deep learning model. The deep learning model may be trained by a supervised method, on deep convolutional neural networks (CNNs). A training data set for supervised learning problem may biological sensor data reviewed and labeled by domain experts (e.g., physicians, clinicians, etc.). In some examples, the training may be implemented by an unsupervised method or a semi-supervised method based on deep CNNs.

The algorithm may be trained by a training set that is specific to a given application, such as, for example classifying a state or condition (e.g., a disease). The training data set for a heart condition may be different from a training data set for a lung condition, for example. In some examples, the training set (e.g., type of data and size of the training set) may be selected such that, in validation, the algorithm yields an output having a predetermined accuracy, sensitivity and/or specificity (e.g., an accuracy of at least 90% when tested on a validation or test sample independent of the training set).

Further, during the processing by the trained algorithm, data from different time periods may be compared, whereby a first set of biological data of a patient over a first time period may be processed and/or compared with and a second set of biological data of the patient over a second time period. As a non-limiting example, a patient with an arrhythmia may transmit recorded ECG data to a server over a period of two years, and for an annual remote consultation, a specialist may process the ECG data recorded over the first year with the ECG data recorded over the second year via a program that uses an expert system or trained algorithm to identify trends, which may determine that the patient's arrhythmia is gradually changing.

Patient biological data that is recorded and transmitted to the computing system may be processed on its own, and/or along with patient data previously transmitted by the patient, or it may be processed (e.g., compared) with control samples and/or patient data transmitted by other patients. For example, during a single remote consultation with a patient, a remote clinician may run an analytics program on ongoing live stream data, to determine a health condition of the patient. Additionally or alternatively, the patient data is compared with historical data from a variety of anonymized patients, thereby determining that the patient is suffering from a particular kind of arrhythmia, and/or the patient's data may be compared with historical data for the patient over the duration of the patient's relationship with the care facility to evaluate a patient's disease progression.

Due to the need to protect the confidentiality of a patient's private healthcare information, the telehealth system 100 may also include technologies and procedures for protecting patient data from any unauthorized access. The receiving device 152 may include a receiver side application 155, which may be used to handle authentication of the receiving device 152. The receiver side application 155 may be a mobile, computer, or web application. For example, a request for authentication may be sent by receiver side application 155 on the receiving device 152 to the monitoring device app 134 on the transmitting device 132. Authentication of the receiving device 152 by the monitoring device application 134 and receiver side application 155 may be performed in conjunction with a web server 190, which may be communicatively connected to the server 180. The authentication of the receiving device 152 may include logging into a hospital account and/or network, and/or any other procedures established by a medical care facility within which the receiving device 152 is being used. The authentication of the receiving device 152 may also include an explicit request for a patient's permission for a clinician to access their personal health information. Further, the receiver side application 155 may be used to assign a secure temporary web address where the data transmitted by the transmitting device 132 may be accessed by the receiving device 152 in order to prevent any security breaches.

As an example, a patient may initiate a previously scheduled remote consultation (e.g., from their home) by placing the monitoring device 102 on their chest and opening up the monitoring device app 134 on the transmitting device 132 (e.g., an iPad). The transmitting device 132 may receiver biological sensor data of the patient sensed by the plurality of sensors of the monitoring device 102 via the monitoring device app 134, which it may begin streaming to the server 180. Separately, a remote caregiver (e.g., clinician) located at a care facility may turn on the receiving device 152 (e.g., a PC), open the receiver side application 155, and request authentication from the server to view the patient data being transmitted by the transmitting device 132. The server 180 may receive the request for authentication from the receiving device 152 via the web server 190, and send the request for authentication to the transmitting device 132 for a response from the patient. If the patient sends a message back to the server 180 accepting the request for authentication originally sent from the receiving device 152 and the web application 155, the server then proceeds to generate a secure web address where the patient data may be safely and confidentially accessed by the caregiver. The secure web address is then sent to the receiving device 152, where it is received by the receiver side application 155. At the same time, the server 180 sends a request to the web server 190 to serve up one or more web pages with the biological sensor data sensed by the plurality of sensors of the monitor device 102 at the secure web address, which the caregiver may then access by clicking on a link in the receiver side application 155. The authentication process is described in further detail below in relation to FIG. 4. In some examples, the caregiver's credentials may be automatically authenticated based on log-in information entered via the receiver side application 155.

Referring now to FIG. 2A, a telehealth peer-to-peer live stream system (telehealth P2P system) 200 is shown for use in situations in which the transmitting device 132 and the receiving device 152 of telehealth system 100 are able to communicate directly via a peer-to-peer (P2P) connection. For transmitting and receiving devices, P2P technologies may be employed to facilitate direct communication between the transmitting device 132 and the receiving device 152 of telehealth system 200 instead of or in addition to communicating via the server 180. An advantage to communicating via P2P technologies in such circumstances may be that data transmission may be faster, thus reducing any latency in the display of time series data on the receiving device 152.

In an embodiment, the monitoring device app 134 and the receiver side app 155 may first try to establish a P2P connection between the transmitting device 132 and the receiving device 152. If the monitoring device app 134 and the receiver side app 155 fail to establish a P2P connection between the transmitting device 132 and the receiving device 152 (for example, due to security reasons where a certain port is not available), the monitoring device app 134 on the transmitting device 132 may connect to the receiver side app 155 on the receiving device 152 via the server 180. Network 210 may be a hospital or clinic network in situations in which a patient is receiving remote care from a caregiver within a care facility where the caregiver is located.

For example, a patient who is suspected of being infected with a coronavirus such as COVID19 may receive treatment for a heart condition in an area of the hospital that is under quarantine, from a clinician located in a research unit of the same facility that is not under quarantine. Thus, the clinician may perform an analysis of the patient's heart condition with the aid of real-time ECG and/or auscultation information without exposing herself to the virus. Alternatively, a nurse may take auscultation and ECG measurements in a waiting room or exam room for the physician/clinician to view prior to meeting the patient (e.g., along with temperature, pulse, and blood pressure that are typically checked prior to a consultation). In such cases, when the patient activates the monitoring device app upon entering the hospital, the monitoring device app may determine that the receiving device (e.g., the specialist caregiver's device) and the patient's transmitting device (e.g., the patient's smart phone) may both communicate over the hospital network, and may attempt to establish a P2P connection. If the P2P connection fails, the monitoring device app on the patient's smart phone may attempt to connect to the specialist caregiver's device over the Internet, via the server 180.

Telehealth peer-to-peer live stream system 200 may include a P2P server 220 that establishes a direct connection between the transmitting device 132 and the receiving device 152. The P2P server 220 may include a signaling service 222 that establishes a signal channel between the transmitting device 132 and the receiving device 152, for sending session description information as part of the P2P connection process. Session description information is sent using the using the Session Description Protocol (SDP).

In some embodiments, the P2P server 220 may also include a Session Traversal Utilities for NAT (STUN) service 224 and/or a Transversal Using Relays around NAT (TURN) service 226. In other embodiments, the STUN and/or TURN services may be provided by third-party STUN and TURN servers. The role of STUN and/or TURN services is to create lists of candidate addresses/ports, using STUN/TURN protocols and the Interactive Conductivity Establishment (ICE) standard, for generating lists of potential addresses/ports for the transmitting device 132 and the receiving device 152 to connect with each other (referred to herein as "ICE candidates"). The STUN service allows a device to discover its public IP address and the type of Network Address Translator (NAT) it is behind on networks where firewalls and NAT's might have specific policies that do not allow direct messaging via SDP. In the event that the STUN service 224 fails to provide potential addresses and/or ports for establishing a connection between the transmitting device 132 and the receiving device 152, the TURN service 226 may be used to relay traffic between the transmitting device 132 and the receiving device 152.

For example, once the monitoring device 102 is in position and is streaming patient data from the sensor unit 120 to the transmitting device 132, the receiving device 152 may use the P2P server 220 to request a connection with the transmitting device 132 over the network 210 in order to access the patient data. The receiving device 152 may initiate a peer-to-peer connection with the transmitting device 132 by creating an SDP description that includes all the information about the receiving device 152's proposed configuration for the connection (e.g., an "offer"). When the offer is created, the receiving device 152 may request from the STUN service that it generate a list of ICE candidates, meaning potential addresses/ports available for the receiving device 152 to communicate over a public network, which will be ordered according to messaging efficiency (e.g., the first ICE candidate will be the one that represents the fastest connection with the receiving device 152). The receiving device 152 may use the signaling service 222 to send its offer to the transmitting device 132, with its first ICE candidate attached. In response, the transmitting device 132 may create its own session description with its own proposed configuration for the connection (e.g., an "answer"), and request from the STUN service that it generate its own list of ICE candidates. The transmitting device 132 may then use the signaling service 222 to send its answer to the receiving device 152. In this way, the transmitting device 132 and the receiving device 152 iteratively negotiate over the signal channel provided by the signaling service 222 until an ICE candidate pair is determined that allows the transmitting device 132 and the receiving device 152 to directly connect with each other. Once the transmitting device 132 and the receiving device 152 have communicated their preferred addresses and ports and session descriptions, the transmitting device 132 may initiate transmission of biological sensor data to the receiving device 152, and there is no further communication with the P2P server 220 and/or the STUN/TURN services 224 and 226, respectively.

If, on the other hand, the STUN service 224 is unable to provide an appropriate list of ICE candidates to either the receiving device 152 or the transmitting device 132, either device may request from the TURN service 226 a relay address that may be used to relay data between the receiving device 152 and the transmitting device 132. If the TURN service 226 is unable to provide a relay address for relay data between the receiving device 152 and the transmitting device 132, a P2P connection may not be established between the receiving device 152 and the transmitting device 132, and data transfers between the transmitting device 132 and the receiving device 152 may be carried out via the server 180, as described above in reference to FIG. 1.

Turning to FIG. 2B, an example procedure for establishing a P2P connection is illustrated wherein the interactions between a transmitting device, a receiving device, a signaling service, a STUN server, and a TURN server are broken down into 5 communication types. The transmitting device, receiving device, signaling service, STUN server, and TURN server may be the same as or similar to the transmitting device 132, the receiving device 152, the signaling service 222, the STUN service 224, and the TURN service 226 of the telehealth peer-to-peer live stream system 200 of FIG. 2A.

In some cases, the communication types may correspond to different stages of the P2P connection procedure, while in other cases the communication types may correspond to different informational exchanges within a single stage of the P2P connection procedure. In this example, a direct connection 250 is first attempted to be established between the transmitting device and the receiving device, via a STUN server. As mentioned earlier, the STUN server may be part of the P2P server 220 of the telehealth peer-to-peer live stream system 200 of FIG. 2A, or it may be a public STUN server implemented outside of the telehealth peer-to-peer live stream system 200. It will be appreciated that while in this example the P2P connection request is initiated by the transmitting device, in other examples the P2P connection may be initiated by the receiving device. During this stage of the P2P connection procedure, the transmitting device requests a public address from the STUN server where the receiving device can connect to it. The STUN server may also be used to provide a public address for the receiving device for connection by the transmitting device. The STUN server determines the public addresses to be used by the transmitting device and the receiving device during this stage and transmits it back to the requesting device (e.g., in this example the transmitting device).

If the STUN server is unable to provide public addresses for the transmitting device and the receiving device to establish a direct P2P connection, then in a second stage of the P2P connection procedure a relay connection 252 may be established between the transmitting device and the receiving device via a TURN server. As mentioned earlier, the TURN server may be part of the P2P server 220 of the telehealth peer-to-peer live stream system 200 of FIG. 2A, or may be a private TURN server implemented outside of the telehealth peer-to-peer live stream system 200. In order to establish the relay connection 252, the transmitting device requests a channel from the TURN server via the TURN protocol. The TURN server subsequently provides a relay channel to the transmitting device, which may be used by the transmitting device to relay data to the receiving device via a P2P connection established over the relay channel.

In the next stage of the P2P connection procedure, the transmitting device and the receiving device iteratively negotiate which addresses and ports will be used for the transmitting device to connect to the transmitting device and/or vice versa. To initiate this negotiation, the transmitting device sends an offer to the receiving device with information for establishing the P2P connection. The information for establishing the P2P connection sent to the receiving device may be logically separated into application layer information 254 and ICE layer information 256. The application layer information 254 includes session descriptions and associated data used to describe the data that is going to be transmitted. The ICE layer information 256 includes the preferred candidate addresses and ports for establishing the P2P connection (e.g., an ICE candidate). When the transmitting device transmits an offer for a P2P connection to the receiving device, both the application layer information 254 and the ICE layer information 256 are included in the offer. When the receiving device receives the offer, the receiving device responds by sending its own offer back to the transmitting device, which includes its own ICE layer information (e.g., the preferred addresses and ports to be used for establishing the P2P connection with the receiving device). This stage of the P2P connection procedure ends when the transmitting device and the receiving device both accept ICE candidates from each other that definitively establish the ports and addresses that will be used in order to transmit the data. Once the transmitting device and the receiving device have valid addresses for each other, the P2P connection is established and a data transfer stage 258 begins in which data is transferred from the transmitting device to the receiving device (e.g., the biological sensor data discussed in reference to FIG. 2A).

It will be appreciated that the examples mentioned herein are for illustrative purposes, and any type of server or technology capable of connecting two hosts in a P2P arrangement may be used by the telehealth peer-to-peer live stream system 200 without departing from the scope of this disclosure.

Returning to FIG. 2A, as described above in relation to server 180 of telehealth system 100, the receiving device may send a request for authentication to the P2P server 220, which the P2P server 220 may send to the transmitting device 132 for a response by the patient. Upon receiving the request for authentication from the P2P server 220, the patient may accept the authentication request on the transmitting device 132, with the acceptance being communicated back to the P2P server 220. The P2P server 220 may then establish a direct peer-to-peer connection between the transmitting device 132 and the receiving device 152 as described above, whereby real-time or near real-time biological sensor data may be transmitted securely from the transmitting device 132 to the receiving device 152 without any further intervention of the P2P server 220. In an embodiment, real-time biological sensor data may be displayed on the receiving device 152 via the receiver side application 155, obviating the need for the server 182 establish a secure web address where the patient data may be accessed via the procedure discussed above with respect to telehealth system 100. In other embodiments, the receiver side app 155 may not be used, and the real-time data may be transmitted via the HTTPS protocol, allowing it to be rendered in a browser on the receiving device 152. Similarly, the real-time patient data may be displayed on the transmitting device 132 via the monitoring device app 134. Thus, the elimination of the server 180 from the connection process allows real-time patient data to be transmitted faster and more efficiently, with less latency.

Apart from the direct P2P communication facilitated by P2P server 220, the transmitting device 132 and the receiving device 152 may also communicate with server 180 via network 170 in order to access recorded streams and analytics functionalities of the telehealth system 100. The transmitting device 132 may record patient data streams and transmit them to the server 180 to be stored in recorded streams database 186 and processed by analytics engine 184 as described above in relation to FIG. 1. Results generated by the analytics engine 184 may subsequently be sent to the transmitting device 132 via the monitoring device app 134 and the receiving device 152 via the receiver side app 155, to be accessed by the patient and/or transmitting caregiver and the receiving caregiver, respectively.

For example, a nurse in an emergency room may administer the monitoring device 102 to a patient who is concerned he may be having a heart attack. The nurse may open the monitoring device app 134 on the transmitting device 132 (e.g., a smart phone) to receive ECG and heartbeat time series data streamed from the audio sensor 122 and the ECG sensor 124 of the monitoring device 102, which subsequently starts streaming the time series data to the server 180. At the same time, the transmitting device 132 may establish a P2P connection with a receiving device 152 located elsewhere in the hospital (e.g., a clinician's smart phone) via the P2P server 220, as discussed above. In an embodiment, the P2P server 220 may request from the patient, via the transmitting device 132, permission for the clinician to access the patient's data. In other embodiments, the P2P server may connect with the server 180 in order to request that the server 180 authenticate the session via the procedure mentioned in telehealth live streaming system 100.

Upon reviewing the patient's data on the receiving device 152, the cardiologist may determine that the patient is not having a heart attack. However, they may wish to run a program on the analytics engine 184 to compare a 10 second sample of the ECG time series data with N samples taken from the patient over the past year, in order to determine whether a heart condition may have developed. The cardiologist may then send a request to the server 180 over the network 170 (e.g., the Internet) to access the recorded streams database 186 to view the patient's previous ECG samples. The server 180 may then send a request for permission to the transmitting device 132, and the emergency room nurse may respond to the server 180 that the patient has provided his permission, whereupon the server 180 sends a message to the receiving device 152 that the cardiologist has been granted permission to access the patient's personal data. The cardiologist may then send a request from the receiving device 152 to the analytics engine 184 on server 180 to run a program in which a neural network compares a sample of the ECG time series data, already being streamed to the streaming engine 182 by the monitoring device 102, with N samples stored in recorded streams database 186 from regular consultations over the previous year, and output trend information along with any suggested diagnosis. The server 180 may then send the trend information and suggested diagnosis to the receiving device 152 via a secure web address as discussed above in relation to the telehealth system 100, to be viewed by the receiving cardiologist on web application 155 and by the emergency room nurse on web application 135. Additionally, the receiving cardiologist may store any recordings and/or any results returned by the analytics engine 184 in the patient electronic medical record (EMR).

Results from the analytics engine 184 may also be requested by the receiving device 152 directly from the transmitting device 132, with no direct connection between the receiving device 152 and the server 180. For example, for security reasons it may be desirable for the receiving device 152 not to have direct access to data stored on the server 180. In some embodiments, the receiving device 152 may send a request for a recording or analytics to the monitoring device app 134 of the transmitting device 132, which may process the request. The analytics engine 184 may then return any results back to the monitoring device app 134 on the transmitting device 132, which in turn may send the results to the receiver side app 155 on the receiving device 152.

Thus, FIGS. 1, 2A and 2B illustrate systems and methods by which real time biological sensor data, as well as other patient data, may be transmitted from one or more monitoring devices located at the point of care to a remote caregiver specialized in cardiology, via devices such as their own phones, tablets, or computers. Further, the telehealth system 100 and telehealth peer-to-peer live stream system 200 are robust enough to handle a variety of use cases, including situations where a remote patient requests and receives treatment from their home, or receives treatment from a clinic where the attending physician may request the support of a remote clinician, or where for reasons of logistics, efficiency, or safety it is not desirable for a clinician to be present at the point of care, or any other similar situation. The telehealth system 100 and telehealth peer-to-peer live stream system 200 also provide for the efficient transmission of data over long distances via the Internet, as well as over short distances.

Figure 3:
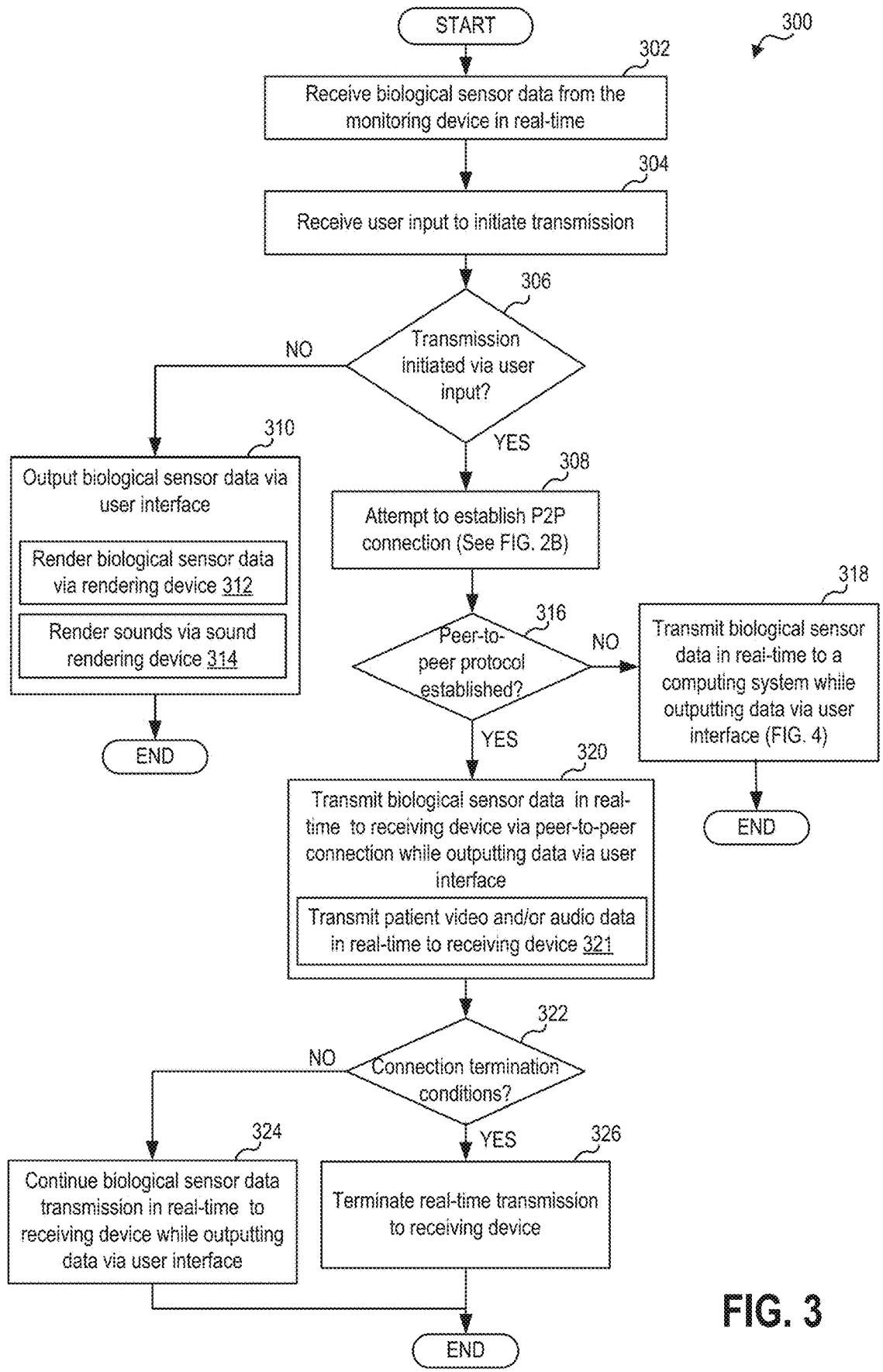
FIG. 3 is a high-level flowchart illustrating an example method for live streaming data via a central server or peer-to-peer technology.

Referring now to FIG. 3, an example method 300 describes how patient data collected via a monitoring device may be streamed from a transmitting device to a receiving device within a telehealth system. The telehealth system described in relation to method 300 may be the telehealth system 100 described in relation to FIG. 1, or the telehealth peer-to-peer live stream system 200 described in relation to FIG. 2A. Instructions for carrying out method 300 may be executed by a processing system of the transmitting device (e.g., the processor 142 of the transmitting device 132 shown in FIGS. 1 and 2A and described above) based on instructions stored in a non-transitory memory of the transmitting device (e.g., memory 144 shown in FIG. 1 and described above) in conjunction with input provided to the transmitting device via a user interface (such as user interface device 148 shown by FIG. 1 and described above) by a user of the transmitting device (e.g., a patient, or an attending caregiver).

At 302, method 300 includes receiving a live stream of biological sensor data (e.g., auscultation and ECG data) from the monitoring device in real-time. The monitoring device may be the same as or similar to the monitoring device 102 of the telehealth systems 100 and 200. As discussed above at FIG. 1, the biological sensor data may include one or more of auscultation sound data (one or more of heart, lung, and bowel sound data), ECG data, PPG data, blood pressure data, otoscope data, and temperature data from corresponding sensors implemented in the monitoring device or one or more peripheral monitoring devices or a combination thereof. It will be appreciated that other physiological data of the patient from additional health monitors may also be integrated with the transmitting device such that the other physiological data are received in real time or near real-time at the transmitting device, and are within the scope of disclosure.

As an example, the monitoring device may have been placed upon the patient's chest and turned on by the user, who may be the patient or physician health care provider at the point of care, and the auscultation, ECG, and/or other patient data may be acquired via one or more sensors located in the monitoring device. The transmitting device may receive the live stream via BLE or similar PAN network technology, as described above. Once the monitoring device is paired with the transmitting device to initiate Bluetooth and is turned on, the monitoring device may automatically start streaming biological sensor data to the transmitting device, where it may be viewed by the user (e.g., the patient or the healthcare provider at the point of care). For example, the biological sensor data may be viewed on the transmitting device via an installed app such as the monitoring device app 134 of telehealth system 100. As discussed above, the monitoring device app 134 may be a mobile, a web, or a computer application.

At 304, method 300 includes receiving user input to initiate transmission of the received biological sensor data to a receiving device. The receiving device may be the same as or similar to the receiving device 152 of telehealth system 100. The user input may be registered via one or more GUI control elements such as radio buttons, checkboxes, selectors, etc., and may include information that is manually entered in, for example, into fields displayed within an app installed on the transmitting device. The user input may explicitly indicate the recipient of the streamed data via an email address, phone number, or any other identifier with a messenger service capable of reliably communicating with a remote device. Alternatively, a recipient may be selected from a list of preauthorized recipients (e.g., clinicians), whereby the preauthorized recipients' chosen means of be contacted and/or receiving information may be accessed from a memory device (e.g., the memory 114 of the monitoring device 102, or the memory 144 of the transmitting device 132). For example, in telehealth system 100, a patient seeking a remote consultation to resolve whether or not she has pneumonia may place the monitoring device 102 over her lungs and turn it on, open up the monitoring device app 134 on the transmitting device 132 (e.g., her iPhone), type in the email address of her remote caregiver in a field displayed in the monitoring device app 134, and select a "send" button to send an invitation to the remote caregiver to access her streaming data. Alternatively, she may place the monitoring device 102 on her chest and turn it on, open up the monitoring device app 134 on her iPhone, select a cardiovascular specialist from a drop-down menu of caregivers appearing in the monitoring device app 134, and select a "send" button to send an invitation to the remote cardiovascular specialist to access her streaming data.

In some cases, no transmission may be initiated, and the monitoring device app may be used for displaying the biological sensor data of the patient on the transmitting device for local use by the patient or attending healthcare provider, as discussed below.

At 306, method 300 includes determining whether the transmission of the biological sensor data to the receiving device has been initiated based on a user request. If no input is detected from the user to initiate the transmission of the biological sensor data, method 300 proceeds to 310, and the biological sensor data is output to the transmitting device via the monitoring device app installed on the transmitting device. Outputting biological sensor data includes, at 312, rendering biological sensor data via visual rendering device (e.g., display portion of the UI 148 of the transmitting device 132), to be viewed by the user (e.g., the patient, the attending healthcare provider, and/or caregiver), and at 314, rendering the sounds on a sound rendering device (e.g., the transmitting device 132) to be listened to by the user (e.g., patient and/or attending physician and/or caregiver). When one or more types of sound data are obtained, the user, via respective control button on the user interface may select (e.g., by clicking the respective control button) which sound they wish to hear, and the selected sound may be rendered via the sound rendering device. In some embodiments, the visual rendering device and the sound rendering device may be one or more separate devices, for example, headphones, external speakers, external monitor, etc., or the monitoring device itself, or on any other device capable of rendering visual displays and/or sounds. The examples described herein are listed for illustrative purposes, and any type of device may be used to render the biological sensor data without departing from the scope of this disclosure.

In one example, the biological sensor data may include auscultation data (e.g., heart sounds) and ECG data obtained in a time synchronized manner from an audio sensor and an ECG sensor of a monitoring device, such as monitoring device 102 at FIG. 1. The ECG waveform may be rendered on a referential scale on the display portion of the user interface of the transmitting device, the referential scale based on the corresponding time synchronized heart sounds. Simultaneously, the heart sounds may be rendered via the sound rendering device coupled to the transmitting device.

Returning to 306, if user input has been received to initiate the transmission of the biological sensor data to the receiving device at 306, method 300 proceeds to 308, and at 308, method 300 includes attempting to establish a P2P connection. As described earlier, establishing a P2P connection with the receiving device may entail connecting with a signaling server (e.g., the P2P server 220 of telehealth system 200), as described earlier with respect to FIGS. 2A and 2B.

At 316, method 300 includes determining whether a P2P connection has been established. If it is determined at 316 that a P2P connection has been established with the receiving device, method 300 proceeds to 320. At 320, method 300 includes transmitting the biological sensor data to the receiving device, in real-time, via the P2P connection. Simultaneously, the processor outputs the biological sensor data via the monitoring device app for display via the visual rendering and sound rendering devices described at 312 and 314.

Further, at 321, the method 300 includes transmitting patient video and/or audio data in parallel with the biological sensor data via the P2P connection. The patient video data may be obtained via a camera, such as camera 171 at FIG. 1, communicatively coupled to the transmitting device, and the patient audio may be obtained via a microphone, such as microphone 173 at FIG. 1, communicatively coupled to the transmitting device. The camera and/or the microphone may be accessed via the monitoring device app on the transmitting device. Responsive to the user initiating acquisition and transmission of the patient video and/or audio, the patient video and/or audio data may be acquired by the camera and/or the microphone respectively, and transmitted, in real-time or near real-time, to the receiving device, in parallel with the biological sensor data via the P2P connection. Further, the patient video and/or audio may be transmitted in a time synchronized manner with biological sensor data. In this way, patient video and/or audio data is integrated with the biological sensor data, and the patient video and/or audio data are transmitted in real-time or near real-time along with biological sensor data, via the transmitting device, to the receiving device. Furthermore, via the P2P connection, the transmitting device may receive remote user video and/or audio data from the receiving device, in real time or near real-time, that are rendered via the visual and/or audio rendering interface respectively of the transmitting device. This enables a remote user (that is, a remote clinician or a remote health care provider) to monitor biological sensor data of the patient in real-time or near real-time while communicating the patient (via video and/or audio communication) simultaneously in real-time.

In addition to receiving biological sensor data of the patient and communicating with the patient, the remote user may initiate artificial intelligence based analysis of the received biological sensor data from the receiving device. In particular, the remote user receiving and viewing the biological sensor data at the receiving device, may initiate a health condition analysis on the real-time or near real-time biological sensor data. The health condition analysis request may be transmitted to the transmitting device from the receiving device via the P2P connection. Details of processing at the health condition analysis request the transmitting device and subsequent artificial intelligence based analysis is further described below with respect to FIGS. 5 and 7 respectively.

Returning to 320 and 321, upon transmitting biological sensor data and patient video and/or audio data, the method 300 proceeds to 322. At 322, method 300 includes determining whether conditions have been met for terminating the connection. For example, the connection may be terminated if a threshold value for a duration of the session has been reached without an authentication request having been made and/or a confirmation having been received, or if the transmitting device determines that the receiving device is no longer displaying data via the receiver side app installed on the receiving device (e.g., if the app is closed), or the connection may be terminated manually via user input (e.g., by closing the monitoring device app on the transmitting device). In some examples, a user may request termination of real-time biological sensor data transmission, via a power off control button on the monitoring device app, for example. Responsive to the user requested termination, the method may include determining if a current request (e.g., for artificial intelligence based analysis, for recording and storing biological sensor data, for additional processing on a recording) is in progress, and if so, the termination request may not be executed until the current request is completed. The current request may originate from the receiving device or the transmitting device. Details of receiving device and/or transmitting device initiated requests and the corresponding processing of biological sensor data based on the requests will be further discussed with respect to FIGS. 5 and 7.

If it is determined at 322 that conditions for termination have been met, method 300 proceeds to 326, and the transmitting device terminates the real time transmission of patient data to the receiving device. Alternatively, if it is determined at 322 that conditions for termination have not been met, method 300 proceeds to 324, and the processor continues to transmit the biological sensor data real-time or near real-time to the receiving device, while also outputting the data to the monitoring device app installed on the transmitting device for display via the rendering and sound rendering devices described at 312 and 314.

Returning to 316, if at 316 it is determined that a P2P connection could not be established (e.g., because one or both of the peers is behind a symmetric NAT), method 300 proceeds to 318. At 318, the processor connects to the receiving device via a centralized computing system (e.g., the server 180 of the telehealth live streaming system 100) and the processor transmits the biological sensor data in real-time to the computing system, while also outputting the data to the monitoring device app installed on the transmitting device to be rendered via the rendering and sound rendering devices described at 312 and 314. The transmission of patient data from the transmitting device to the receiving device via a computing system as discussed in further detail below with respect to FIG. 4.

In one embodiment, the transmitting device or the central server, via its respective processors, may monitor a signal quality of the biological sensor data received from one or more of the monitoring device and the at-home peripheral monitoring devices. Responsive to the signal quality of the biological sensor data greater than a threshold, the transmitting device or the central server may automatically initiate artificial-intelligence based analysis of the biological sensor data and/or initiate storage of the biological sensor data. The signal quality may be, in one example, a cumulative signal quality of biological sensor data, wherein an individual signal quality of data from each device or each sensor (from each monitoring device and peripheral device) is utilized to determine the cumulative signal quality. In this example, responsive to the cumulative signal quality greater than a threshold cumulative signal quality, the transmitting device may initiate AI based analysis of the biological sensor data and/or store a portion of biological sensor data (with signal quality greater than the threshold). In another example, the individual signal quality of sensor data from each device or sensor may be monitored with respect to the respective sensor's signal quality threshold, and when the individual signal quality of the sensor data is greater than the respective sensor's signal quality threshold, AI based analysis of the sensor data may be automatically initiated and/or a portion of the sensor data may be stored onto a medical record of the patient. In some examples, when there are more than one sensors in a device, if the sensor data from any one of the sensors in the device is greater than the respective sensor's signal quality threshold, then AI based analysis of biological sensor data from the device may be initiated and/or biological sensor data may be stored onto the patient's medical record. Similarly, each device's signal quality may be monitored individually, with respect to the device or individually, with respect to the sensors, or any combination thereof. As a non-limiting example, for a monitoring device such as monitoring device 102 having ECG and audio sensors, at the transmitting device, upon receiving ECG data and audio data, the transmitting device may monitor a respective signal quality of both the ECG and audio data. Responsive to the respective signal quality of ECG data or audio data greater than a respective signal quality threshold, the transmitting device may automatically initiate storage of biological sensor data (ECG and audio data) and/or AI-based analysis of the biological sensor data (both ECG and audio data) from the monitoring device 102, which may include transmitting biological sensor data to the central server for AI-analysis. However, in some examples, if signal quality of ECG data is greater than an ECG quality threshold but audio data is less than an audio data quality threshold, only ECG data may be analyzed and/or stored, and vice-versa.

The signal quality of biological sensor data may be based on a signal quality metric corresponding to the sensor data. As a non-limiting example, for waveform data, such as phonocardiogram signals and ECG signals, signal quality may be based on at least one or more of amplitude characteristics and frequency characteristics of the waveform data. Further, the signal quality of biological sensor data may be based on efficiency of biological sensor data transmission from the monitoring device to the transmitting device or from the transmitting device to the server, depending on the device that performs the signal quality check. The efficiency of biological sensor data transmission may be determined based on a packet loss rate, for example. Thus, two levels of signal quality check may be performed to initiate automatic AI-based analysis. As a non-limiting example, at the transmitting device, responsive to receiving biological sensor data from a monitoring device, a transmission efficiency (e.g., packet loss rate) may be evaluated, and further a signal quality metric of the received biological sensor data (either individual sensor data or cumulative) may be determined, and the automatic initiation of AI-based analysis and/or storage of the received biological sensor data may be based on the transmission efficiency and the signal quality metric being greater than the respective thresholds.

While some of the above examples for automated AI analysis and/or storage based on signal quality are performed at the transmitting device, in some embodiments, such as a central server based system in FIG. 1, the signal quality analysis may be performed at a processor of the central server. As biological sensor data is streaming in real-time or near real-time via the central server, the central server may evaluate the signal quality of the biological sensor data that it received from the transmitting device, and responsive to the signal quality of the biological sensor data greater than the threshold, the central server may automatically initiate AI analysis on the biological sensor data and/or store a portion of the biological sensor onto a patient's medical record.

Figure 4:
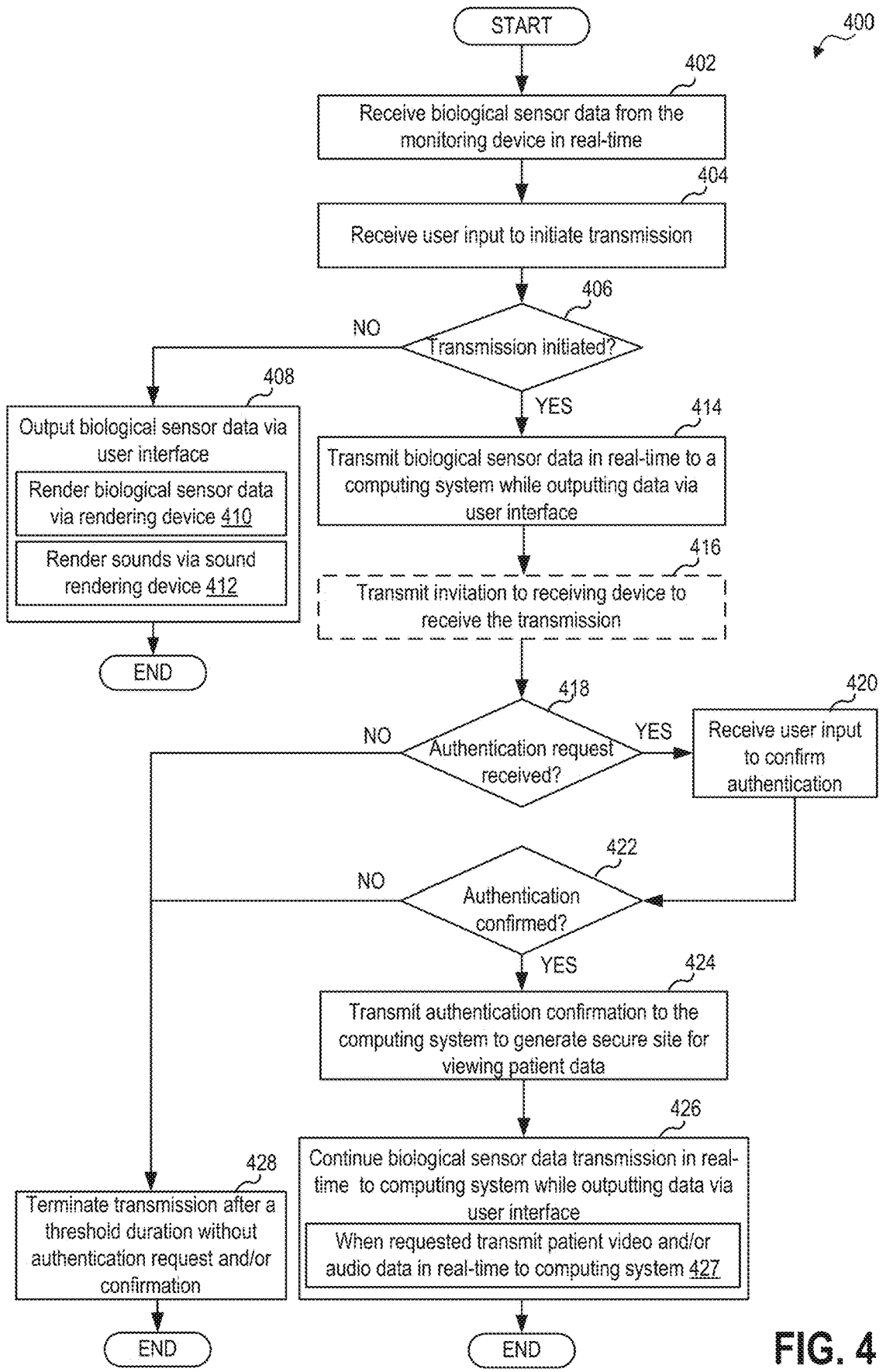
FIG. 4 is a high-level flowchart illustrating an example method for live streaming data from a monitoring device to a receiving device and authenticating the receiving device via a transmitting device communicatively coupled to the monitoring device.

Referring now to FIG. 4, an example method 400 describes how biological sensor data collected via a monitoring device may be streamed from a transmitting device to a receiving device via a central computing system in a telehealth system, such as telehealth system 100 described in relation to FIG. 1. Instructions for carrying out method 400 may be executed by a processing system of the transmitting device (e.g., the processor of the transmitting device 132 shown in FIG. 1 and described above) based on instructions stored in non-transitory memory of the transmitting device (e.g., memory 144 shown in FIG. 1 and described above) in conjunction with input provided to the transmitting device via a user interface (such as user interface device 148 shown by FIG. 1 and described above) by a user of the transmitting device (e.g., a patient, or an attending caregiver).

At 402, method 400 includes receiving biological sensor data from the monitoring device in real-time or near real-time, as explained in relation to FIG. 3 above. As with the previous method 300 of FIG. 3, the biological sensor data may include one or more of auscultation sound data (one or more of heart, lung, and bowel sound data), ECG data, PPG data, blood pressure data, otoscope data, and temperature data acquired via a monitoring device such as the monitoring device 102 of the telehealth system 100 and/or one or more peripheral health monitoring devices. At 404, method 400 includes receiving user input to initiate transmission of biological sensor data to the receiving device. The receiving device may be the same as or similar to the receiving device 152 of telehealth system 100. For example, in telehealth system 100, an attending physician treating a patient with heart disease may select a cardiac specialist from a list of caregivers displayed via a drop-down menu in the monitoring device app 134, and select a button that sends an invitation to the cardiac specialist to access and review biological sensor data streamed from the transmitting device 132 to the receiving device 152.

At 406 the method 400 includes determining whether transmission has been initiated. As in FIG. 3 above, if no input is detected from the user to initiate the transmission of the biological sensor data, method 400 proceeds to 408, and the processor renders the biological sensor data on the transmitting device via the monitoring device app (e.g., monitoring device app 134) installed on it. At 410, method 400 includes rendering the biological sensor data on the display screen of a rendering device, (e.g., the UI 148 of the transmitting device 132) to be viewed by the patient and/or attending physician and/or nurse, and at 412, method 400 includes rendering the acquired sounds (e.g., heart sounds, lung sounds, bowel sounds etc.) on a sound rendering device (e.g., the transmitting device 132) to be listened to by the patient and/or attending physician and/or nurse.

If at 406 it is determined that a transmission has been initiated by a user, method 400 proceeds to 414, and the processor proceeds to transmit the biological sensor data in real-time or near real-time to a computing system, while also outputting the data to the user interface of the transmitting device, as indicated at 408, 410, and 412. The computing system may be the same as or similar to the server 180 of the telehealth system 100. The biological sensor data transmitted to the computing system may be processed by the transmitting device prior to being sent to the computing system. For example, the biological sensor data acquired by a monitoring device (such as the monitoring device 102 of the telehealth system 100) may be digitized, filtered, encoded, compressed, and encrypted at the transmitting device for transmission to the receiving device. It will be appreciated that the examples of the types of processing listed herein are for illustrative purposes, and any other types of processing may be included without limiting the scope of this disclosure. The biological sensor data may be tagged along with additional data such as patient metadata, information regarding the type of analysis to be carried out, data acquired from one or more of the at-home monitoring devices and/or audio/video sources (e.g., the peripheral at-home monitoring devices 175 and/or peripheral audio/video sources 174 of telehealth system 100), or any other type of data relevant to the patient or the patient's condition.

Once the transmitting device initiates the transmission of patient data to the computing system, at 416 method 400 includes sending an invitation to the receiving device to access the transmitted data. In an embodiment, the invitation may be sent from a monitoring device app on the transmitting device (e.g., monitoring device app 134) to a monitoring device app on the receiving device (e.g., receiver side app 155). For example, a user (e.g., a patient or clinician at point of care) may select a receiving device corresponding to a remote user (e.g., a remote caregiver or specialist) from a preapproved list of potential recipients displayed in a drop-down menu on the monitoring device app installed on the transmitting device, and send an invitation to the recipient via a control element (e.g., a button). Alternatively, the user may manually enter in an email address, phone number, etc. to send the invitation as described above in reference to FIG. 3. In other embodiments, the invitation may be in the form of an email, a text message, direct message on a social networking platform, or via any other reliable third-party messaging application. In still other embodiments, an invitation may be automatically sent to a preselected recipient upon initiation of data streaming, or no invitation may be sent. For example, a patient who is waiting in a consultation room to be seen by a specialist caregiver may initiate transmission of the patient's biological sensor data but not send an invitation, as the specialist caregiver may be expecting the transmission as result of the scheduled visit.

When the invitation is received at the receiving device, or in the event that no invitation is received but the remote user of the receiving device (e.g., a clinician) is aware that biological sensor data is being transmitted, in order for the user of the receiving device to access the transmitted data, the remote user may have to request authorization to view the patient's personal data. The authentication procedure may involve a verification of the remote user of the receiving device and/or explicitly requesting permission from the patient. For example, a remote clinician who wishes to access live streaming data from a remote patient may send an authentication request to the computing system (e.g., server 180 of telehealth system 100), which may request that the clinician log into their account on a hospital network, and may relay the authentication request to the transmitting device. The authentication procedure performed on the computing system (e.g., the server 180) is discussed in further detail below with respect to FIG. 6.

At 418, method 400 includes determining whether an authentication request has been received from the receiving device. If an authentication request has been received at 418, method 400 proceeds to 420, and the processor receives input from the user (e.g., a patient or attending caregiver) to confirm the authentication of the recipient (e.g., a remote caregiver or specialist). For example, a patient using the transmitting device 132 of telehealth system 100 may receive a notification of an authentication request via a pop-up display element in the monitoring device app 134, and may confirm the authentication of the recipient by selecting a control element such as a button on the pop-up display element.

At 422, method 400 includes determining whether the authentication has been confirmed by the user of the transmitting device (e.g., the patient or attending caregiver). If the transmitting device does not receive an authentication request at 418, or if the transmitting device receives an authentication request but does not receive confirmation of the authentication from the user at 422, method proceeds to 428, and the processor terminates the transmission after a threshold duration has been exceeded without having received an authentication request and/or an authentication confirmation. Alternatively, if the request for authentication received at 418 is confirmed at 422, method 400 proceeds to 424, and the processor transmits the authentication confirmation to the computing system (e.g., server 180), which generates a secure site (e.g., via a web server such as web server 190 of telehealth system 100) where the recipient may view the patient data via the receiving device. The management of the authentication process by the computing system is discussed in further detail below with respect to FIG. 6.

At 426, method 400 includes continuing to transmit the biological sensor data in real time to the computing system in order for it to be subsequently relayed to the receiving device, while also outputting the data to the user interface of the transmitting device as indicated at 408, 410, at 412. Further, at 427, method 400 includes transmitting, in real-time or near real-time, one or more of patient audio and video, acquired via one or more of microphone, such as microphone 173 at FIG. 1, and camera, such as camera 171 at FIG. 1, from the transmitting device to the computing system. The transmission of one or more of patient audio and video may be initiated in response to a user request at the transmitting device. For example, the user may initiate, via the monitoring device app on the transmitting device, live stream of patient audio and/or video. The patient audio and/or video may be initiated at any time along with biological sensor data transmission, for example, prior to authentication of receiver at step 414, during authentication, or after authentication at step 427. As discussed above, the patient audio and/or video may be transmitted in parallel with the biological sensor data and in a time-synchronized manner with respect to the biological sensor data. Further, the transmitting device may receive live stream data of remote user audio and/or video, via the computing device, when the receiver audio and/or video transmission is initiated from the receiving device. The receiver audio and/or video may be rendered via sound rendering device coupled to the transmitting device and display portion of the UI of the transmitting device in real-time or near real-time. In this way, via the central server, real-time audio and/or video communication between the transmitting device and receiving device is integrated with real-time biological sensor data transmission to the receiving device.

Figure 5:
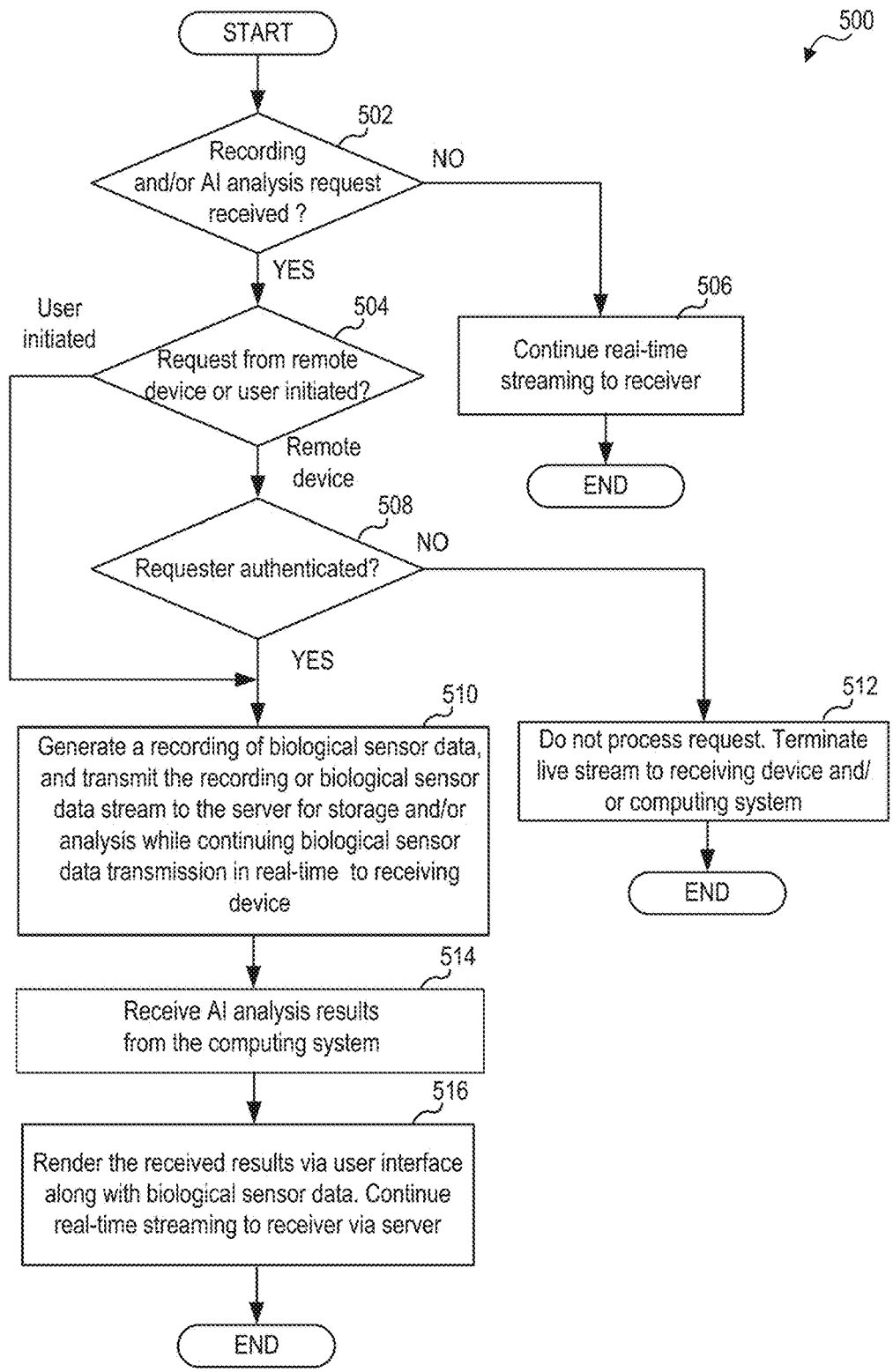
FIG. 5 is a high-level flowchart illustrating an example method for live streaming where a receiver initiates recording of data for analysis.

Referring now to FIG. 5, an example method 500 describes, in a telehealth system (e.g., the telehealth system 100 described in relation to FIG. 1), a process by which real-time data analytics may be requested from one or more of a transmitting device (e.g., the transmitting device 132) and a receiving device (e.g., the receiving device 152) via a central computing system (e.g., server 180). Instructions for carrying out method 500 may be executed by a processor in the transmitting device (e.g., the processor 142 shown in FIG. 1 and described above) based on instructions in non-transitory memory (e.g., memory 144 shown in FIG. 1) of the transmitting device in conjunction with input provided to the transmitting device via a user interface (such as user interface device 148 shown by FIG. 1 and described above) by a user of the transmitting device (e.g., a patient, or an attending caregiver) and/or input from a receiving device (e.g., receiving device 152) in communication (via central server based connection as shown in FIG. 1 or via peer-to-peer connection as shown in FIGS. 2A and 2B) with the transmitting device.

At 502, method 500 includes determining whether a request has been received at the transmitting device. The request may be received from the receiving device via a communication link (peer-to-peer or central server based) or from a user input at the transmitting device. While the present example is discussed with respect to a single request, two or more requests may be received and processed accordingly (e.g., based on any of priority of the request, order received, etc.). The request may be for a recording of biological sensor data and/or an analysis of the biological sensor data. The request for analysis may include an AI based analysis of the biological sensor data.

The biological sensor data is acquired by the monitoring device and transmitted, in real-time or near real-time, from the transmitting device to the receiving device, and the request for recording and/or analysis is with respect to the biological sensor data that is being transmitted in real-time to the receiving device. For example, the receiving device and/or the transmitting device may initiate a recording of the biological sensor data and/or analysis of the biological sensor data in order to save the current biological data for future reference and perform health condition analysis of the patient respectively.

In one example, the transmitting device may key in on a message type indication in the receiver transmitted data (e.g., JSON encoded message) sent from the receiver and execute actions based on the message type. Thus, the transmitting device may determine a type of request based on the message key, and execute corresponding action as described further below.

As discussed above, the biological sensor data may include one or more of auscultation sound data (one or more of heart, lung, and bowel sound data), ECG data, PPG data, blood pressure data, otoscope data, and temperature data from corresponding sensors implemented in the monitoring device or one or more peripheral monitoring devices or a combination thereof. In one example, the request may include recording and/or analysis on one or more subsets of biological sensor data that is currently transmitted in real-time. Each subset of the biological sensor data may include sensor data from a sensor of the monitoring device or any of the peripheral health monitoring devices, or sensor data from a subset of combination of sensors of the monitoring device and the peripheral health devices. For example, the request may include analysis on a subset of biological sensor data that includes ECG data alone or auscultation data alone or a combination of ECG and auscultation data. Thus, the request may be with respect to data acquired from any sensor or any combination of sensors. In some examples, the request may be with respect to all the biological sensor data transmitted in real-time.

In one example, a remote clinician may receive the biological sensor data at the receiving device in real-time from a patient transmitting the biological sensor data acquired via the monitoring device. At the receiving device, the remote clinician may view (e.g., via a display of the receiving device) a real-time rendering of ECG data, and hear (e.g., via a pair of ear phones coupled to the receiving device) a real-time rendering of heart sounds in a time-synchronized manner with respect to the rendering ECG data. Additionally, the remote clinician may view real-time rendering of PPG data, otoscope data, and temperature data of the patient. The remote clinician may wish to analyze the ECG and heart sound data, and as such, may initiate a request from the receiving device, via a control button (e.g., via a GUI of receiver side application 155, a corresponding GUI of a web browser, etc.) to perform an analysis on the ECG and heart sound data. It will be appreciated that the receiver side application may include request options (via one or more control buttons displayed on the UI of the receiver side app) for the clinician to request analysis and/or recording any for any combination of the biological sensor data received that the receiving device. While the above example illustrates receiver initiated request, the request for analysis and/or recording on any combination of biological sensor data may be initiated at the transmitting device (e.g., via the monitoring device application)

When an analysis request is received, the corresponding analysis may be performed on the biological sensor data by an analytics engine. The analytics engine may be the same as or similar to analytics engine 184 of the telehealth system 100, and may perform AI analysis on the biological sensor data. In this way, the telehealth system described herein enables a remote clinician to perform AI analytics on the biological sensor data in real-time. An example method for how the analysis of real-time patient data may be carried out by a computing system (e.g., the server 180) is discussed in further detail below with respect to FIG. 7.

If no requests for patient data recordings and/or analysis are received at 502, method 500 proceeds to 506, and the processor continues to stream the biological sensor data in real time to the receiving device (e.g., via the computing system, to be subsequently relayed to a secure web address where the receiving device may access it or directly via peer-to-peer connection). Alternatively, if a request for a recording and/or analysis of patient data is received at 502, method 500 proceeds to 504, and the processor determines whether the request was made from a remote device (e.g., the receiving device 152) or whether the request was made from the transmitting device. If at 504 it is determined that the request was made from the remote device, method 500 proceeds to 508, and the processor determines whether the requester (e.g., the user of the receiving device 152) has been authenticated or not, according to the procedure described earlier with respect to FIGS. 1-4. If at 508 it is determined that the requester has not been authenticated, method 500 proceeds to 512, and the processor does not process the request, and in some examples, may terminate the live stream to the receiving device and/or to the computing system.

Alternatively, if is determined at 504 that the request was either initiated by the transmitting device, or that the request was from an authenticated receiving device at 508, method 500 proceeds to 510. At 510, the method includes generating a recording of the biological sensor data and transmitting the recording to the server for storage and/or analysis, while continuing to transmit the biological sensor data to the receiving device in real time as described above. Alternatively, in one embodiment, the method includes transmitting the real-time or near real-time biological sensor data stream from the transmitting device to the server along with an indication for storage and/or analysis depending on the request initiated. For example, in response to an analysis request, instead of generating a recording, the transmitting device may send the biological sensor data stream to the server, and the server may either generate a second recording of the biological sensor data stream for subsequent processing with the AI algorithm or process the biological sensor data stream with the AI algorithm. Similarly, in response to a recording request, alternative to generating the recording at the transmitting device, the transmitting device may send the real-time biological sensor to the server for generating a third recording for storage.

When recording is generated at the transmitting device, in one embodiment, the recording of biological sensor data may be automatically generated responsive to the request. In other embodiments, the processor may notify the user that a request has been received, and prompt them to initiate a recording (e.g., via a GUI of the monitoring device app on the transmitting device). In still other embodiments, the processor may notify the user that they are requested to generate a recording at a later time, and may schedule a reminder to indicate when the recording is to be initiated, such as alert sound or notification generated on the transmitting device.

As discussed above at 502, the request (from the receiving device and/or the transmitting device) may indicate one or more types of biological sensor data, a subset of biological sensor data, any combination of subset of biological sensor data, or all biological sensor data for processing. The biological sensor data indicated in the request (from the transmitting device or the receiving device) may be alternatively referred to herein as a requested biological sensor data. The request may further indicate the type of action that may be performed on the requested biological sensor data. The type of action may include one or more of recording for storage (e.g., in an EMR of the patient) and/or analysis. In some examples, the type of action may include additional processing (e.g. filtering, annotation, etc.) of the requested biological sensor data. In some examples, the request may further include a duration of recording for one or more of the recording for storage, analysis, and additional processing.

When the request includes one or more of the storage, analysis, and additional processing, a recording of the requested biological sensor data may be generated at the transmitting device. For example, in response to a request for one or more of storage, analysis, and additional processing, the transmitting device may automatically generate a recording of the requested biological data that is received at the transmitting device in real-time from the monitoring device.

In some examples, when the request is initiated from the transmitting device, the type of action indicated on the request may include an a power on or power off request for a requested monitoring device from among the monitoring device and the one or more peripheral monitoring devices generating the biological sensor data. When the request includes the power on or off request, one or more corresponding actions may include turning the requested monitoring device ON or OFF. Further, turning the requested monitoring device ON includes establishing a wireless connection between the requested monitoring device and the transmitting device. Further, in response to turning the requested device on, newly acquired data may be acquired from the requested medical device, and transmitted to the receiving device via the transmitting device. For example, the transmitting device may be receiving biological sensor data from one or more monitoring devices (e.g., monitoring device 102 and peripheral devices 175), and may add the requested monitoring device by establishing a wireless connection between the requested monitoring device and the transmitting device and thereby, include data from one or more sensors of the requested device in the real-time transmission of the biological sensor data in response to a power on request. Further, the transmitting device may remove a specified device by terminating a wireless connection between the specified device and the transmitting device, and thereby, stop receiving corresponding data from the specified device in response to a power off request.

In one embodiment, the transmitting device processor may assess or determine local signal quality prior to transmitting the recording or the biological sensor data to the server. For example, the processor may not transmit the recording or the biological sensor data unless the signal quality exceeds a threshold quality. The signal quality may be based on a signal quality metric of the biological sensor data and/or transmission efficiency as discussed above with respect to signal quality based automated initiation of AI analysis at FIG. 3. If the threshold quality has not been met, the processor may continue to monitor signal quality specifically for AI analysis. Thus, a window for analysis may be based on the desired duration of the recording. If the signal quality is below the threshold for a threshold duration, a notification may be sent to the receiving device and/or the transmitting device that the signal quality is low, thus providing an opportunity for the receiver (e.g., a clinician or specialist) to provide any relevant suggestions or indications to the transmitter (e.g., a patient or attending caregiver).

Additionally, when recording is requested for storing and/or AI analysis, some additional pre-processing may be carried out to remove background noise. For example, active noise cancelling parameters may be adjusted in order to reduce unrelated sounds (e.g., someone talking). In this way, by generating the recording at the transmitting device and pre-processing the recording prior to transmitting the recording, server processing time may be saved, and the results may be generated more quickly.

In some embodiments, the server may pre-process the recording prior to storing and/or analysis. Further, in some embodiments, during one condition (e.g., server load greater than a threshold load), the transmitting device may generate and pre-process the recording, while during another condition (e.g., server load less than the threshold load), the transmitting device may send biological sensor data to the server for generating and pre-processing the recording. In still further embodiments, the transmitting device may generate the recording in response to the request, while the server may pre-process the recording prior to storing the recording and/or performing AI analysis on the recording.

In another embodiment, the processor may assess a state or condition of the patient prior to transmitting the recording. For example, the request may indicate that a recording may be initiated upon exceeding a threshold condition, such as a heart rate exceeding 90 bpm, whereby a recording is automatically generated when the condition has been satisfied.

In some examples, the request may further specify one or more additional parameters for the recording, such as what type or types of monitoring to carry out, how long the recording may last, and/or any conditions or guidelines to follow, or any other parameters. For example, the request may specify acquiring an ECG recording of a patient's heart for a specific duration (e.g., 10 seconds, 30 seconds, etc.), or the request may specify acquiring an ECG recording of a patient's heart and heart auscultation data collected simultaneously. In one embodiment, the duration may be specified by entering in a number of seconds. In other embodiments, the duration may be selected from a list of candidate durations. For example, a remote caregiver on the receiving device may select a duration from a list of durations displayed in a drop down menu of the UI of the receiving device (e.g., UI 168 of the receiving device 152), within the monitoring device app. Further, durations that are displayed in a monitoring device app installed either on the transmitting device (e.g., the monitoring device app 134 of telehealth system 100) or on the receiving device (e.g., the receiver side app 155 of telehealth system 100) may be configurable. For example, an attending caregiver on the transmitting device 132 may establish one or more duration options (e.g., 10 seconds, 30 seconds, etc.), such that the duration options may be displayed later within a drop-down menu or similar interactive controls on the monitoring device app for easy selection later. The request may also include conditions or guidelines for acquiring the biological sensor data. For example, the request may specify that a recording must be taken after a specified amount of activity. For example, the request may include a parameter indicating that the patient may engage in activity until their heart rate reaches a threshold level.

When the request includes an analysis request for health condition of the patient, the generated recording of the requested biological sensor data or the real-time or near real-time biological sensor data stream may be transmitted from the transmitting device to the computing device along with an indication to perform artificial intelligence (AI) based analysis to determine health condition of the patient.

When the request includes a storage request, the generated recording of the requested biological sensor data or the real-time or near real-time biological sensor data stream may be transmitted from the transmitting device to the computing device along with an indication to store the recorded biological sensor data in the EMR of the patient.

When the request includes additional processing request, the generated recording or the real-time or near real-time biological sensor data may be transmitted to the computing device along with an indication to perform additional signal processing (e.g., to remove background noise etc.). In some examples, the additional signal processing may be performed at the transmitting device.

In addition to generating a recording, transmitting the recording to the computing system, and simultaneously, transmitting, in real-time, biological sensor data to the receiving device, the transmitting device may continue to output and render real-time biological sensor data on one or more of visual and sound rendering devices coupled to the transmitting device.

Once the recording has been analyzed by the analytics engine in the computing system (e.g., analytics engine 184 of server 180), the results may be transmitted back to the transmitting device, or may be transmitted to the receiving device, or may be transmitted to both devices, as discussed in further detail below with respect to FIG. 7. Thus, at 514 method 500 includes receiving the results of the analysis carried out by the computing system, and at 516, method 500 includes rendering the biological sensor data via visual rendering device (e.g., the UI 148 of the transmitting device 132) to be viewed by the patient and/or attending physician and/or nurse, and/or rendering the auscultation sounds on a sound rendering device (e.g., ear phones coupled to the transmitting device 132) to be listened to by the patient and/or attending physician and/or nurse.

In some examples, if, responsive to a request, the transmitting device transmits a recording of requested biological sensor data to the computing system for analysis, the transmitting device may not allow termination of the session until the recording has been fully analyzed by the analytics engine and the results have been transmitted to the transmitting device and/or the receiving device. For example, the transmitting device may determine completion of requested action based on a completion indication from the computing system. The completion indication from the computing system may be based on the request and may include an indication that a requested analysis has been completed and transmitted to the receiving device, an indication that the recorded biological sensor data is stored in the EMR, etc. As an example, responsive to a request from the transmitting device to terminate the session, the transmitting device may check if a completion indication has been received from the computing system, and if the completion indication is not received, the transmitting device may determine that the requested AI analysis is still in progress, and as such, the session may not be terminated until results have been received from the computing system. In some examples, a notification may be provided to the UI of the transmitting device with an indication of the ongoing AI analysis. The notification may further include a confirmation request asking the user to verify whether they wish to terminate the session and not receive the results of the analysis.

Further, the method 500 may include determining whether the transmitting device and the receiving device are connected via a peer-to-peer connection. If the transmitting device and the receiving device are not connected via a peer-to-peer connection, the method 500 proceeds to 516 to render the results locally and ends. Alternatively, if the transmitting device and the receiving device are connected via a peer-to-peer connection, the processor transmits the biological sensor data in real-time to the receiving device via the peer-to-peer connection along with the results of the analysis, until termination conditions are satisfied.

In some embodiments, the receiver may request continued transmission of a subset of biological sensor data and without remaining biological sensor data. For example, the remote clinician may wish to continue monitoring lung sounds which may be of more relevance to a patient's condition, and may not require real-time monitoring of PPG. Thus, the remote clinician may request via communication link with the transmitting device (which may be either central server based connection or peer-to-peer connection) that the transmitting device may selectively transmit a subset of biological sensor data, which is lung sounds in this example. Responsive to the selective transmission request from the receiving device, the transmitting device may initiate another request from the transmitting device to power off corresponding monitoring devices that do not generate the selected biological sensor data. Thus, in this example, responsive to the selective transmission request from the receiving device, the transmitting device may automatically generate a second request to terminate connection with the PPG sensor while maintaining wireless communication with the monitoring device acquiring the lung sounds.

In some embodiments, the receiving device and/or the transmitting device may initiate multiple requests sequentially or in parallel. For example, the receiving device may initiate a first request for a first AI analysis on a subset of biological sensor data, and based on the result of the first analysis, the receiving device may generate a second request for AI analysis on a second subset of biological sensor data, and a third request for storing recordings of the first subset and/or second subset along with the corresponding AI analysis results.

In this way, the transmitting device may receive one or more requests, including a request for AI analytics, from the receiving device, and process the biological sensor data obtained from one or more of the monitoring device and peripheral devices based on the request.

As an example, a specialist caregiver providing remote care to a patient within a telehealth system may initiate AI analysis of biological sensor data (e.g., ECG and auscultation data) acquired via a monitoring device, via a request sent directly to a transmitting device (e.g., patient side computing device). The system may be configured such that the AI analysis is performed automatically when certain conditions are met. For example, a patient who suspects that they may have a heart condition may initiate a telehealth videoconference session with a remote cardiologist. Upon establishing communication with the patient, the remote cardiologist may view ECG sensor data of the patient and request AI assistance in analyzing ECG data. Particularly, in a telehealth system such as telehealth system 100 or telehealth system 200, the cardiologist may request real-time AI analytics on ECG data streaming from the patient's device. In response to the request, the transmitting device may send a recording of the ECG data or real-time or near real-time data stream to a computing device (e.g., central server) for AI analysis. When the analysis has finished, the results of the AI analysis may be sent to the remote cardiologist during the same telehealth session. Thus, the diagnosis received by the patient from the cardiologist, along with the results of the AI analysis, may be delivered promptly within a single telehealth session, obviating the need for the patient to travel to a clinic, wait in line, see a specialist, undergo testing, and wait for results.

Figure 6:
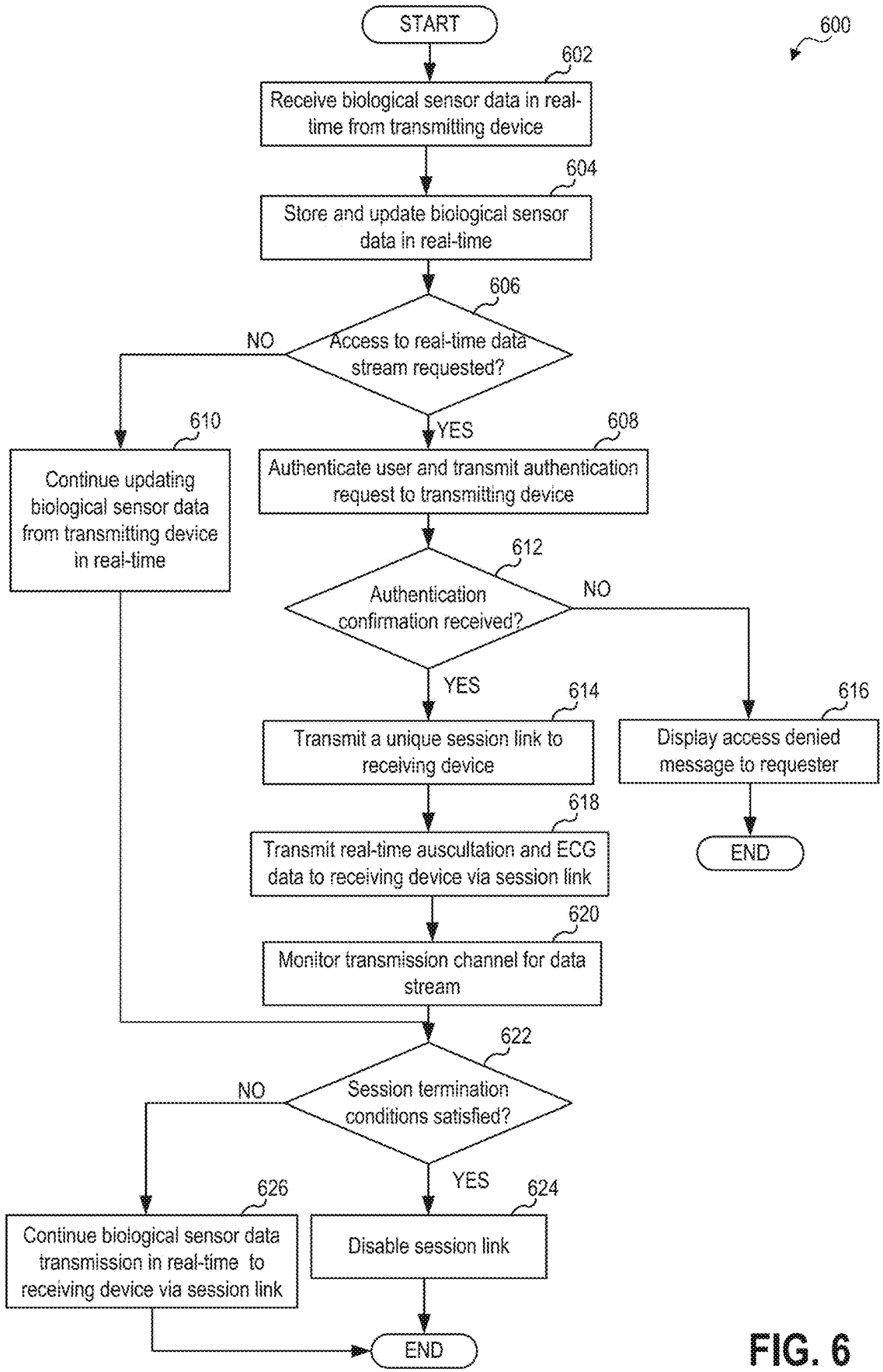
FIG. 6 is a high-level flowchart illustrating an example method for live streaming executed by a server.

Turning now to FIG. 6, an example method 600 describes how a data streaming engine installed on a central computing system (e.g., a server) in a telehealth system handles the process of authenticating a user (e.g., a clinician) who wishes to access real-time biological sensor data via a receiving device, and how the computing system or server handles the secure streaming of biological sensor data from a transmitting device to a receiving device. The telehealth system described in reference to method 600 may be the telehealth system 100, and the data streaming engine may be the same as or similar to the data streaming engine 182 of the server 180 in the aforementioned system. Similarly, the transmitting device and the receiving device may be the transmitting device 132 and the receiving device 152 of telehealth system 100. Instructions for carrying out method 600 may be executed by a processing system of the computing system (e.g., the server 180 of telehealth system 100 described in FIG. 1) based on instructions stored in memory accessible to the data streaming engine. Additionally, the data streaming engine may have access to one or more memories that may be used for temporarily storing live stream patient data (e.g., a memory buffer register on a hard drive) during the process of streaming patient data to a receiving device. Method 600 may be implemented based on instructions stored in non-transitory memory of the computing system, for example, in a physical server, a virtual server operating in a cloud in communication with the telehealth system 100, or any appropriate combination thereof.

As described above in relation to FIG. 1, for the purposes of confidentiality and security it may not be desirable for the transmitting device to directly stream data to the receiving device. Therefore, a computing system (e.g. a server such as server 180) may be used to stream the biological sensor data transmitted by the transmitting device to a temporary private webpage where the receiving device may access it during a secure session. The generation of the temporary private webpage may be carried out in conjunction with a web server, such as web server 190 of telehealth system. An advantage of using a computing system to relay the stream of patient data to the receiving device is that the computing system may ensure that users accessing private patient data have been authenticated (e.g., identified via login credentials) and authorized (e.g., via explicit permission from the patient) to view the data. Further, patient confidentiality may be maintained by ensuring that the patient's private data is accessible at a web location relevant to the current session, and that the data is not available after the duration of the secure session.

At 602, method 600 includes receiving a stream of biological sensor data in real-time from a transmitting device, to be processed by the data streaming engine. In an embodiment, the patient data may be auscultation and/or ECG data. As described above in relation to FIG. 3, when a monitoring device such as the monitoring device 102 of telehealth system 100 is turned on and placed on a patient's body, it may automatically begin to stream the biological sensor data (e.g., the auscultation and/or ECG data) to a Bluetooth-paired transmitting device via a monitoring device app such as monitoring device app 134 of telehealth system 100. At 604, method 600 includes temporarily storing the streaming patient data in one or more data buffers located in the random access memory (RAM) of the computing system. The amount of streaming patient data that may be held in the buffer may depend on the type of data being streamed and the size of the buffer, which may be customized in the data streaming engine based on the anticipated data type. For example, the default size of a first buffer may be 1.5 MB, which may allow 30 seconds of real-time auscultation data to be stored, while the default size of the second buffer may be 2.5 MB, which may allow 20 seconds of real-time ECG data to be stored. When the data buffer is full, the computing system (via the data streaming engine) updates the patient data in real-time, such that the data held in the buffer is always the most recent data received by the computing system. For example, if the data buffer can accommodate 30 seconds of audio data, the data streaming engine updates the data buffer with new streaming data such that the patient data held in the data buffer always corresponds to the last 30 seconds of audio data received.

At 606, method 600 includes determining whether a request has been made to access the real-time data stream by a receiving device (e.g., the receiving device 152 of telehealth system 100). If access to real-time data has not been requested at 606, method 600 proceeds to 610, and the computing system continues to update the biological sensor data received from the transmitting device in real-time, until session termination conditions are met at 622 as described below. Alternatively, if access to real-time data has been requested at 606, method 600 proceeds to 608, and the computing system authenticates the user of the receiving device and transmits an authentication request to the transmitting device. For example, the computing system may request that the user of the receiving device log onto a hospital network, clinic account, or otherwise provide credentials to verify who they are, prior to asking the patient with the transmitting device for explicit permission to grant the user of the receiving device access to his personal data.

At 612, method 600 includes determining whether a confirmation of authentication has been received from the transmitting device (e.g., from the patient), indicating to the computing system that the patient has provided their permission for the user of the receiving device to access their data. If the authentication confirmation is not received at 612, method 600 proceeds to 616, and the computing system displays an access denied message to the requester (e.g., the user of the receiving device), and the method ends. Alternatively, if an authentication confirmation is received at 612, method 600 proceeds to 614, and the computing system transmits a unique session link to the receiving device, which upon selection by the user of the receiving device allows the user of the receiving device to securely access the patient data at a private location (e.g., in a receiver side application such as receiver side application 155 of telehealth system 100). At 618, method 600 includes transmitting the real-time biological sensor data stored in one or more data buffers of the data streaming engine to the receiving device via the session link.

At 620, method 600 includes continuing to monitor the transmission channel for the data stream while the data is being streamed, in order to determine whether to stop the transmission in the event that any termination conditions are met. For example, the transmission may be stopped if the data stream is terminated by the transmitting device, or if the data stream is no longer being accessed by the receiving device, or if the data stream is unavailable for a threshold duration, etc. The termination conditions described herein are listed for illustrative purposes, and any alternative and/or additional termination conditions may be included without departing from the scope of this disclosure. At 622, method 600 includes determining whether any session termination conditions have been satisfied. If a termination condition has been satisfied at 622, method 600 proceeds to 624, and the computing system disables the session link, effectively ending the session. If no termination conditions have been satisfied at 622, method 600 proceeds to 626, and the computing system continues to update the biological sensor data transmission in real-time in its data buffers, and continues to transmit the data stream to the receiving device via the session link.

Figure 7:
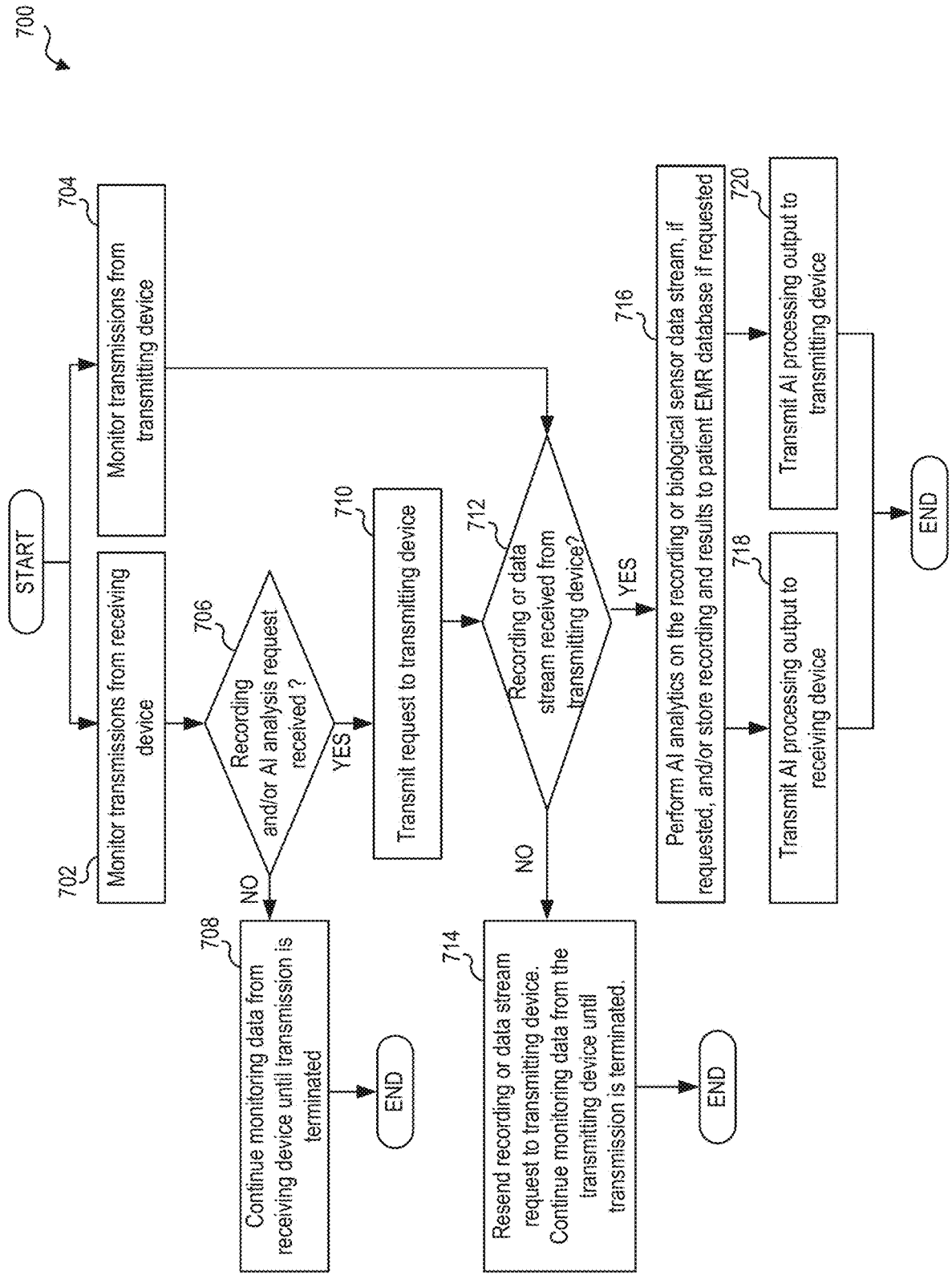
FIG. 7 is a high-level flowchart illustrating an example method for processing data from a live stream responsive to one or more requests.

Referring now to FIG. 7, it shows a high-level flow chart illustrating an example method 700 for processing one or more requests from a receiving device, such as receiving device 152 of telehealth system 100, and/or a transmitting device, such as transmitting device 132 of telehealth system. Specifically, method 700 shows how a computing system (e.g., a server) in a telehealth system handles requests for recordings of streams of patient data and/or requests for analytics (e.g., by AI programs, neural networks, etc.) from either a user of a receiving device (e.g., a clinician) or user of a transmitting device (e.g., a patient or attending caregiver). The telehealth system described in reference to method 700 may be the telehealth system 100. Likewise, the transmitting device and the receiving device may be the transmitting device 132 and the receiving device 152 of telehealth system 100, and the computing system may be the same as or similar to the server 180 of telehealth system 100.

Method 700 is described herein with reference to the system and components depicted in FIGS. 1, 2A and 2B, though it will be understood that the method may be applied to other systems and components without departing from the scope of the present disclosure. Method 700 may be carried out by a computing device, such as server 180, a virtual server operating in a cloud in communication with the telehealth system 100, or any appropriate combination thereof, and may be stored as executable instructions in non-transitory memory of the computing device. In a non-liming example, method 700 may be stored as executable instructions in non-transitory memory of an analytics engine within the computing system (e.g., such as analytics engine 184 of server 180)

The analytics carried out by the analytics engine may include the application of one or more algorithms (e.g., a process or rule for conducting a calculation or other problem-solving operation). An algorithm may take patient data as input, and make a determination in regard to the patient data as result of applying one or more pre-established rules based on evidence-based medicine (e.g., an expert system). For example, an algorithm may take a heart rate as input and determine whether the heart rate is fast or slow by comparing it with pre-established thresholds. The algorithm may also be a trained algorithm that is trained with one or more training sets, which may include data generated from subjects with known physiological or biological states or conditions. The trained algorithm may comprise a machine learning algorithm such as a supervised machine learning algorithm or an unsupervised machine learning algorithm. For example, the trained algorithm may be a neural network or similar artificial intelligence (AI) system that takes biological sensor data as input and processes it in relation to training data in order to output a result. The result may include an assessment of the state or condition of the heart of the patient, a suggested diagnosis, one or more recommendations for follow-up tests or treatment alternatives, an indication of a recurring pattern, an indication of a trend or the growth or abatement of a trend, and/or any other similar indication relevant to diagnosing or treating a condition. The output of the trained algorithm may further comprise displaying a graph, spectrogram, or other representation of recorded biological sensor data streamed from a patient produced as a result of processing the biological sensor data. For example, the output may comprise a prototypical heartbeat sound after removing noises caused by subject motion, device motion, or other reasons in an audio wave form of a heartbeat. In some examples, the output may include an integrated acoustic cardiograph (ACG) report comprising interpretation of ECG data and sound data. The output of the trained algorithm may also comprise a dysfunction score calculated to provide a quantitative metric, description, or prediction of a patient's state or condition. The output of the trained algorithm may also comprise audio feedback that may be heard via the transmitting device and/or receiving device. As described in further detail below, the output may be rendered in a graphical user interface (GUI) of an application (e.g., the monitoring device app 134, or a browser) running on the receiving device, the transmitting device, and/or the monitoring device.

At 702 and 704, method 700 includes monitoring transmissions from the receiving device and transmissions from the transmitting device, respectively. Transmissions from the receiving device monitored at 702 may include one or more of requests for authentication and requests for processing of patient data streams including recording requests and analysis requests. Transmissions from the transmitting device monitored at 704 may include one or more of responses to authentication requests, and real-time biological data streamed to the receiving device such as in a central server—client based connection for biological data transmission, as discussed at FIG. 1. Transmissions from the transmitting device may further include one or more of recordings of biological data (for storage and/or analytics), and analysis requests initiated from the transmitting device.

At 706, method 700 includes determining whether a request has been received from the receiving device for the recording and/or analysis of patient data stream (e.g., biological sensor data) that is currently received, in real-time or near real-time, at the receiving device. If it is determined at 706 that no request for analysis or recording has been received from the receiving device, method 700 proceeds to 708, and the computing system continues monitoring the data from the receiver until the transmission is terminated, for example, in accordance with termination conditions as described above in relation to FIG. 6. Alternatively, if it is determined at 706 that the request for the recording or analysis of the patient data stream has been received from the receiving device, method 700 proceeds to 710, and the computing system transmits the request to the transmitting device. Upon receiving the request from the computing system (that is, the server), the transmitting device may generate a recording of the biological data that is currently live streamed to the receiving device via the computing system. Details of generating the recording at the transmitting device is discussed above at step 510 at FIG. 5.

It will be appreciated that in the event that a peer-to-peer connection is made between the transmitting device and the receiving device as discussed above with respect to telehealth peer-to-peer live stream system 200 of FIG. 2A, the computing system would not be monitoring transmissions from the receiving device. The transmitting device and the receiving device would be to be communicatively coupled via the peer-to-peer connection, whereby any requests for recordings or analytics to be performed on the computing system could be made from the receiving device to the transmitting device via the peer-to-peer connection.

In response to the request, a recording of a patient's data may be generated automatically by the transmitting device (e.g., via a monitoring device app installed on the transmitting device) and transmitted to the computing system for analysis. For example, in telehealth system 200, wherein the transmitting device 132 and the receiving device 152 are communicatively coupled via a peer-to-peer connection, a user (e.g., a clinician receiving live stream data of a patient at the receiving device), may initiate a request for AI based analysis and/or recording on the live stream data of the patient. The transmitting device 132 may receive the request for AI based analysis via the peer-to-peer connection. In response to the request, the transmitting device 132 may automatically generate a recording of the biological data being streamed from the monitoring device 102. The transmitting device may then transmit the recording to the server 180, without interfering with the simultaneous and continuous live streaming of the biological data to the receiving device 152.

In one embodiment, as discussed with respect to FIG. 5, the transmitting device may transmit real-time or near real-time biological sensor data to the computing system for one or more of pre-processing, storage and/or analysis. In an embodiment, if more than one request is received during a live stream session (e.g. one request is received from an attending caregiver via the transmitting device and another request is received from a remote specialist via the receiving device), the requests may each be assigned a priority and executed in order according to their priority. For example, requests from the remote specialist may be prioritized over requests from the attending caregiver, or vice-versa, or requests may be prioritized on a first-come first-served basis, or in any other way. In other embodiments, a user (e.g., a remote or attending caregiver) may be notified of multiple requests and/or prompted to select a request to address and/or prioritize the requests.

Returning to method 700, at 712, method 700 includes determining whether a recording of the biological sensor data stream or biological sensor data stream has been received from the transmitting device (e.g., in response to the request from the computing system at 710 and/or in response to request from the receiving device via peer-to-peer connection). If at 712 it is determined that no recording or data stream has been received, method 700 proceeds to 714, and at 714, the computing system continues monitoring the data from the transmitting device until the transmission has been terminated. In some embodiments, as indicated above, the real-time or near real-time biological sensor data stream may be transmitted from the transmitting device instead of the recording, and responsive to receiving the real-time or near real-time biologicals sensor data stream from the transmitting device, the computing system may perform AI analytics on the real-time or near-time biological sensor data, as discussed below at step 716. Said another way, responsive to an analysis request from one or more of the transmitting device and the receiving device, the computing system may receive real-time or near real-time biological sensor data stream, generate a second recording of the received stream, and perform AI analytics on the second recording. Alternatively, responsive to the analysis request from one or more of the transmitting device and the receiving device, the computing system may receive real-time or near real-time biological sensor data stream, and perform real-time AI analysis with the AI based algorithm. The analysis with the AI based algorithm is further discussed below at step 716. Additionally, in some examples, if the computing system has transmitted the request and a threshold has passed after the request has been transmitted, the computing system may resend the request to the transmitting device. In case of a peer-to-peer connection, the computing system does not send the request, and continues to monitor data from the transmitting device. If at 712 it is determined that a recording or data stream has been received from the transmitting device, method 700 proceeds to 716 in order to perform the requested analytics on the biological data in the recording or on the biological sensor data stream. As described above, the analytics may be performed by an analytics engine such as the analytics engine 184 on server 180 of telehealth system 100.

As part of analytics, a trained artificial intelligence (AI) algorithm may receive the recording as input, wherein the recording may be generated by the transmitting device or the computing device, or receive the biological sensor data stream as input, process the biological data (obtained from the one or more sensors of the monitoring device) in the recording or the biological sensor data stream, and output a health condition result, which may include one or more of a quantitative metric and a description of a health condition of a patient. For example, ECG data and auscultation data from an ECG transducer and an audio transducer of the monitoring device may be processed using a trained AI algorithm. Further, data from any or any combination of the sensors of the monitoring device, and data from sensing modalities of one or more of other health monitoring devices, such as photoplethysmogram (PPG) sensor, blood pressure sensor, otoscope sensor, temperature sensor, and weight sensor, the data including PPG data, blood pressure data, pulse oximetry data, otoscope data, temperature data, and weight data, or any combination thereof may be processed using a trained AI algorithm. Further, data from any sensing modality such as pressure sensors, vibration sensors, force sensors, respiratory monitors or sensors, heart rate monitors or sensors, and intrathoracic impedance monitors or sensors, or combinations thereof may be processed using a trained AI algorithm.

The trained algorithm is described with respect to FIG. 1. Briefly, the trained algorithm may comprise a convolutional neural network. The trained algorithm may correlate diagnostic features to a specific state or condition of a patient. The trained algorithm may correlate a diagnostic feature to a specific state or condition using a frequency resolved analysis. The trained algorithm may compare recorded data (e.g., any data collected by the monitoring device, such as ECG and auscultation data) or real-time or near real-time biological sensor data stream to at least pre-existing data of diseased and/or healthy subjects in a database of the computing system.

The database may include a plurality of datasets (e.g., large datasets). The plurality of datasets may comprise ECG and auscultation data associated with various states or conditions of different subjects or different organs of the same or different subjects. The database may further comprise other data, such as PPG data, blood pressure data, pulse otoscope data, temperature data, weight data, pressure data, vibration data, force data, respiratory data, heart rate data, and intrathoracic impedance data which individually or in combination, may be correlated with a certain state or condition. It will be appreciated that datasets, and hence, data in the database may correspond to data obtained from the monitoring device and/or one or more other health monitoring devices, and may be expanded to include other data corresponding to new sensor modalities as they are added to the telehealth system.

Further, in some embodiments, the request from the receiving device may specify a type of data to be processed by the trained AI algorithm. For example, a clinician remotely monitoring the patient and receiving the live stream biological data from the various sensors and sensor combinations may request, via a corresponding web, mobile, or computer application of the receiving device, AI algorithm processing on a desired data. The desired data may be a subset of biological data received and monitored via the receiving device. As a non-limiting example, the desired data for AI algorithm processing may be ECG and auscultation data. Accordingly, the request from the receiving device may include an indication of the type of data for processing by the AI trained algorithm. The transmitting device may then generate a recording of the desired data, and transmit the recording of the desired data to the computing device for processing by the AI trained algorithm. Alternatively, the transmitting device may transmit the biological sensor data stream to the computing device, which may be analyzed by the AI algorithm. For example, the computing device may generate a server side recording of the biological sensor data stream that may then be analyzed with the AI algorithm or the computing device may analyze the real-time or near real-time biological sensor data stream with the AI algorithm. While the above example illustrates a request and corresponding AI processing on ECG and auscultation data, any biological data or any combination of biological data discussed above that are streamed in real-time or near real-time at the receiving device may be selected (by the clinician) for AI algorithm processing, a corresponding result that correlates to health condition assessment based on the desired data may be generated by the computing device as output. In some examples, an output of the trained algorithm may additionally include an indication of the type of data that was used as input to the AI trained algorithm.

After performing AI algorithm processing on the recording or on biological sensor data stream, at 718, method 700 includes transmitting an output (that is, a result) of the AI processing to the receiving device, and at 720 method 700 includes transmitting the output of the AI processing to the transmitting device. In some embodiments, the transmission of the output of the AI processing to the receiving device and the transmitting device may be simultaneous. In other embodiments, the output of the AI processing may be transmitted to the receiving device prior to the transmitting device, or the output of the analytics may be transmitted to the transmitting device prior to the receiving device. In still other embodiments, the output of the AI processing may be transmitted only to the receiving device, or only to the transmitting device. The output may include an audio clip, a visual message or a combination thereof. The output of the AI processing may be displayed in a graph, spectrogram, or other representation of the recorded biological data. The output of the trained algorithm may be displayed, on a display interface of the transmitting device and/or receiving device, for example as a graph, spectrogram, or other representation of biological data. The output may further include an audio output indicating a determination (e.g., diagnosis) of health condition of a patient by AI processing or a combination thereof. As a non-limiting example, the output may be provided by playing audio recordings which may convey algorithm findings (e.g., directly) to the user's ear(s). In some examples, the output may include an integrated acoustic cardiograph (ACG) report comprising interpretation of ECG data and sound data.

In some examples, the output of the trained algorithm may be rendered via the monitoring device in addition to rendering the output via the transmitting and the receiving device. The rendering may include one or more of a visual feedback and an audio feedback that may be heard over an audio output interface (e.g., earpiece) coupled to the monitoring device.

Thus, the telehealth systems and methods described herein provide an AI-enabled telehealth platform that remote clinicians may utilize to analyze real-time biological sensor data during live streaming telehealth sessions.

In this way, responsive to an analysis request from one or more of the transmitting device and the receiving device, the computing system may perform AI analysis on the recording sent by the transmitting device, or perform AI analysis on real-time or near real-time biological sensor data stream sent by the transmitting device. In order to perform AI analysis on real-time or near real-time biological sensor data stream, the computing system may generate a second recording of the biological sensor data stream or perform real-time AI analysis on the biological sensor data stream (without generating a recording). Similarly, responsive to a storage request, the computing system may either store recorded data sent from the transmitting device or generate a server side recording and store the generated server side recording. As discussed above, in some embodiments, the recording or the biological sensor data stream may be pre-processed at one or more of the transmitting device and the server prior to analysis or storage depending on the type of request.

In one example, a method for live streaming from a monitoring device may comprise acquiring biological sensor data of a patient via a plurality of sensors of the monitoring device; transmitting, in real-time, the biological sensor data to a transmitting device; transmitting, in real-time, a data stream including the biological sensor data from the transmitting device to a receiving device; initiating, via a computing device, an authenticated session for a user via an application executed at the receiving device to access the data stream; during the authenticated session, responsive to receiving an analysis request from the receiving device, performing, at the computing device, patient condition analysis using an artificial intelligence based algorithm. The method further includes wherein the artificial intelligence based algorithm uses the real-time data stream or a recording of the data stream as input. The method further includes wherein the recording is generated at the transmitting device or the computing device. The method further includes wherein the real time data stream or the recording is pre-processed using one or more signal processing algorithms at the transmitting device or the computing device.

Thus, in response to an analysis request, the transmitting device may send a recording to the computing device for analysis or in response to an analysis request, with the real-time or near real-time biological sensor data stream, a second recording of the biological sensor data may be generated at the computing device and analyzed with the AI algorithm, or the real-time biological sensor data may be analyzed by the AI algorithm.

The technical effect of the telehealth systems and methods described herein is improved disease diagnostic performance and efficiency, and patient health information security in the field of telemedicine. For example, by enabling a remote clinician to perform AI analysis on real-time biological sensor data, disease screening and diagnosis is improved. As AI results are provided to the remote clinician while the remote clinician is receiving and monitoring real-time biological sensor data, the AI analysis increases confidence in the remotely generated real-time biological sensor data, and as such, the remote clinician is able to make diagnosis more quickly with greater confidence. Further, by using the transmitting device at the patient-side to process requests from the clinician, personal health information security is improved. Furthermore, as pre-processing is done at the transmitting device, processing speed of the AI algorithm is improved and thus, multiple requests from different receiving devices are processed with higher efficiency.

Turning to FIG. 8A, it shows a monitoring device 800 comprising a housing 805, which encases sensors and control circuitry. The monitoring device 800 includes a first electrical sensor comprising a first electrode 810A and a second electrode 810B. Electrodes 810A and 810B may be physically separated by a distance to facilitate measurement of electrical signal from a subject. For example, electrodes 810A and 810B may be ECG transducer electrodes, which may measure electrical signals from a patient resulting from depolarization of the heart muscle during a heartbeat. In the illustrated example, the first electrode 810A and the second electrode 810B include contact pads for obtaining ECG data. The monitoring device 800 further includes a second sensor 812 that includes a surface for obtaining audio data. The second sensor 812 may include one or more piezoelectric ("piezo") units for collecting audio data.

The monitoring device may additionally comprise user controls such as button 814. Button 814 may control the intensity of a monitored signal to be transmitted to a user.

Button 814 may comprise a positive end and a negative end, such that when the positive end (e.g. the upper portion) of the button is depressed, a signal amplitude is increased, and when a negative end (e.g. the lower portion) of the button is depressed, a signal amplitude is decreased. A signal amplitude may comprise a volume of an amplified audio signal. The audio signal may be transmitted wirelessly to an earpiece of a user (such as a healthcare provider or the patient). In some examples, the audio signal may be transmitted to a transmitting computing device (e.g., mobile device) wirelessly coupled to the monitoring device 800.

FIG. 8B shows the back of the monitoring device of FIG. 8A. The monitoring device 800 may comprise additional user controls such as button 820. Button 820 may be used to stop and start measurement of data by the monitoring device. Button 820 may be actuated by a user. It may be possible to stop or start measurement without actuation of button 820, such as by controlling collection through a computing device. The shape and design of sensor housing 805 may facilitate a subject's comfort during monitoring a state or condition of a subject. Additionally, the shape and design of sensor housing 805 may facilitate a secure fit against a variety of patient body types and shapes in order to improve sensor contact and with adequate sensor geometry.

While the monitoring device 800 shows two sensor modalities, it will be appreciated that the monitoring device may include a plurality of sensor modalities. Each of the plurality of sensor modalities may include various types of sensors, such as ECG sensors, audio sensors, temperature sensors, pressure sensors, vibration sensors, force sensors, respiratory monitors or sensors (e.g., a device, device part, or sensor capable of measuring a respiration rate), heart rate monitors or sensors, intrathoracic impedance monitors or sensors (e.g., a device, device part, or sensor capable of measuring an intrathoracic impedance), and/or other types of sensors. The sensors may be part of the monitoring device. In some cases, the sensors may be coupled with or otherwise configured to be used in combination with the monitoring device and/or the computing device. The one or more sensors may be sensors of any kind, shape, form, or material.

The monitoring device 800 may comprise one or more analog-to-digital converters (not shown) to digitize ECG signals and/or audio signals to detected by the ECG electrodes (810A and 810B) and the second sensor 812. The monitoring device 800 may further include signal processing circuitry (not shown) to filter and condition detected signals. Signal processing circuitry may include one or more filters (not shown) and one or more encoders (not shown).

The monitoring device 800 may be utilized by a patient to obtain biological sensor data (that is ECG data and/or auscultation sound data in this example), which may be transmitted to a transmitting device in real-time via a wireless communication link, such as BLE. The transmitting device may transmit the received biological sensor data in real-time to a remote receiving device for remote monitoring by a clinician as described above. Another example monitoring device is shown in FIG. 9.

Turning to FIG. 9, an example device 900 for contact-less monitoring of a patient is shown. Device 900 may be configured as a digital stethoscope for wirelessly obtaining auscultation sounds (heart sounds, lung sounds, bowel sounds etc.). The device 900 includes a resonator 901 that is configured to be placed on a body of a patient, and collect audio data (that is, auscultation data) from the body of the patient. The resonator may include, for example, a piezoelectric unit and circuitry for collecting the audio data. The resonator 901 may further include circuitry with a communication interface that may be in communication (wired or wireless communication) with a transmitting unit 902 that includes a button 903. The device 900 may further comprise earpieces 904. The earpieces 904 may be used to listen to audio data as they are being generated. The earpieces 904 may also be used to provide audio feedback generated by the trained algorithm to the user or the healthcare provider. Upon the user pressing the button 903, audio data may be collected from the body of the patient and stored in memory and/or transmitted to a transmitting computing device (e.g., mobile device) in communication with the transmitting unit 902. As discussed above, the transmitting computing device may transmit the received audio data in real-time to a remote receiving device at a different physical location than the device 900 for remote monitoring by a remote clinician.

The disclosure also provides support for a method for streaming acquired biological sensor data of a patient from one or more medical devices, comprising: transmitting, in real-time or near real-time, the acquired data, via a transmitting device wirelessly coupled to the one or more medical devices, to a receiving device, rendering, in real-time or near real-time, the transmitted data at the receiving device, and responsive to one or more signals from the receiving device, performing one or more corresponding actions on the acquired biological sensor data, wherein the one or more corresponding actions include processing the acquired biological sensor data using an artificial intelligence algorithm. In a first example of the method, the acquired biological sensor data includes one or more of auscultation sound data, electrocardiogram (ECG) data, photoplethysmogram (PPG) data, blood pressure data, otoscope data, temperature data, and weight data, and wherein the one or more medical devices and the transmitting device are wirelessly coupled. In a second example of the method, optionally including the first example, the method further comprises: acquiring, at the transmitting device, one or more patient audio data via a microphone and patient video data via a camera, the microphone and the camera communicatively coupled to the transmitting device, transmitting, in real-time or near real-time, the one or more patient audio data and patient video data in parallel with the acquired biological sensor data. In a third example of the method, optionally including the first and second examples, rendering at the receiving device includes displaying, at a display interface of the receiving device, one or more of a result of processing the acquired biological sensor data using the artificial intelligence algorithm, the result indicating a health condition of the patient, one or more biological waveforms based on the acquired biological data, and patient video while outputting audio through an audio output interface of the receiving device, the audio including the result of processing the acquired data, one or more of heart sounds based on the acquired data and patient audio, and wherein the one or more biological waveforms, patient video, heart sounds, and patient audio are rendered in a time synchronized manner. In a fourth example of the method, optionally including the first through third examples, the method further comprises: rendering, in real-time or near real-time the acquired biological sensor data at the transmitting device. In a fifth example of the method, optionally including the first through fourth examples, transmitting in real-time or near real-time to the receiving device includes transmitting the acquired biological sensor data to the receiving device via a central server system. In a sixth example of the method, optionally including the first through fifth examples, transmitting in real-time or near real-time to the receiving device includes transmitting the acquired biological sensor data to the receiving device via a peer-to-peer connection. In a seventh example of the method, optionally including the first through sixth examples, the one or more signals include a power on or power off request for a requested medical device of the one or more medical devices, and the one or more corresponding actions include turning the requested medical device on or off, and when the one or more signals include the power on request, establishing a wireless connection between the requested medical device and the transmitting device, and transmitting acquired data from the requested medical device to the transmitting device. In an eighth example of the method, optionally including the first through seventh examples, the one or more signals include a recording request, and the one or more corresponding actions include generating a recording of the acquired biological sensor data at the transmitting mobile device or a computing device communicatively coupled to the transmitting mobile device, and storing the recording at the computing device. In a ninth example of the method, optionally including the first through eighth examples, processing the acquired biological sensor data using artificial intelligence algorithms is performed in response to an analysis request from the receiving device, and wherein processing the acquired data using the artificial intelligence algorithm includes transmitting the acquired biological sensor data or a recording of the acquired biological sensor data to a computing device, analyzing, at the computing device, the transmitted biological sensor data or the recording utilizing a trained artificial intelligence based algorithm, and providing a result of the analysis via one or more of the transmitting device and the receiving device. In a tenth example of the method, optionally including the first through ninth examples, processing the acquired biological sensor data using the artificial intelligence algorithm is performed in response to a signal quality of the acquired biological sensor data greater than a threshold.

The disclosure also provides support for a method for live streaming from a monitoring device, comprising: acquiring biological sensor data of a patient via a plurality of sensors of the monitoring device, transmitting, in real-time, the biological sensor data to a transmitting device, transmitting, in real-time, a data stream including the biological sensor data from the transmitting device to a receiving device, initiating, via a computing device, an authenticated session for a user via an application executed at the receiving device to access the data stream, during the authenticated session, responsive to receiving an analysis request from the receiving device, performing, at the computing device, patient condition analysis using an artificial intelligence based algorithm. In a first example of the method, the computing device is a part of a client-server network, and wherein transmitting the data stream to the receiving device includes transmitting the acquired data to the receiving device via the computing device. In a second example of the method, optionally including the first example, transmitting the data stream to the receiving device includes transmitting the acquired data to the receiving device via a peer-to-peer connection. In a third example of the method, optionally including the first and second examples, the biological sensor data includes one or more of auscultation sound data, electrocardiogram (ECG) data, photoplethysmogram (PPG) data, blood pressure data, otoscope data, temperature data, and weight data. In a fourth example of the method, optionally including the first through third examples, the method further comprises: at the transmitting device, rendering the biological sensor data, in real-time, via one or more of a sound rendering device coupled to the transmitting device and a display interface of the transmitting device, and at the receiving device, during the authenticated session, rendering the biological sensor data, in real-time, via one or more of a second sound rendering device coupled to the receiving device and a display interface of the receiving device. In a fifth example of the method, optionally including the first through fourth examples, the method further comprises: during the authenticated session, responsive to receiving a recording request from one or more of the mobile device and receiving device, initiating a recording of the data stream. In a sixth example of the method, optionally including the first through fifth examples, a result of the analysis is rendered at one or more of the transmitting device and the receiving device while rendering the biological sensor data.

The disclosure also provides support for a medical monitoring system, comprising: one or more monitoring devices, each including one or more sensors for obtaining biological data of a patient, a transmitting device wirelessly coupled to the one or more monitoring devices, and a computing device implemented by one or more processors, the one or more processors communicatively coupled to the transmitting device and a receiving device, and configured with instructions in non-transitory memory that when executed cause the one or more processors to: receive, in real-time, a data stream including the biological data from the one or more monitoring devices via the transmitting device, initiate an authenticated session for a user to access the data stream via the receiving device, during the authenticated session, transmit the biological sensor data, in real-time, to the receiving device, during a first condition of the authenticated session, when a first message is received from the user via the receiving device, process the data stream in real-time based on the first message, and during a second condition of the authenticated session, when a second message is received from the transmitting mobile device, process the data stream or a first recording of the data stream received from the transmitting device based on the second message, wherein the first message received from the receiving device includes a first artificial intelligence (AI) analysis request, wherein the second message from the transmitting device includes a second AI analysis request. In a first example of the system, the computing device is further configured with instructions in non-transitory memory that when executed cause the one or more processors to: in response to the first AI analysis request, perform a health condition analysis on a portion of the data stream or a second recording of the data stream, the second recording generated at the computing device, and transmit a result of the health condition analysis to the receiving device while transmitting the biological sensor data, in real-time, to one or more of the receiving device and the transmitting device, and in response to the second AI analysis request, perform a second health condition analysis on another portion of the data stream or the first recording of the data stream received from the transmitting device, and transmit a second result of the second health condition analysis to one or more of the receiving device and the transmitting device. In a second example of the system, optionally including the first example, the biological sensor data includes one or more of auscultation sound data, electrocardiogram (ECG) data, photoplethysmogram (PPG) data, blood pressure data, otoscope data, temperature data, and weight data, and wherein the computing device is configured with further instructions in non-transitory memory that when executed cause the one or more processors to: receive, in real-time or near real-time, one or more patient audio data and patient video data, from the transmitting device, and transmit, in real-time or near real-time, the one or more patient audio data and patient video data in parallel with the biological sensor data, to the receiving device.

The disclosure also provides support for a method, comprising acquiring biological sensor data from one or more medical devices, transmitting, in real-time, the acquired biological sensor data to a transmitting device; transmitting, in real-time, a data stream including the acquired biological sensor data from the transmitting device to a receiving device; and responsive to a signal quality of the acquired biological sensor data greater than a threshold, processing the biological sensor data using an artificial intelligence algorithm and/or saving the biological sensor data as a recording.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for streaming acquired biological sensor data of a patient from one or more medical devices, comprising:
responsive to a connection request from a receiving device, establishing a wireless connection between a requested medical device of the one or more medical devices and a transmitting device, and wirelessly transmitting the acquired biological sensor data from the requested medical device to the transmitting device;
transmitting, in real-time or near real-time, the acquired biological sensor data via the transmitting device the receiving device;
rendering, in real-time or near real-time, the transmitted biological sensor data at the receiving device; and
responsive to one or more signals from the receiving device, performing one or more corresponding actions on the acquired biological sensor data;
wherein the one or more corresponding actions include processing the acquired biological sensor data using an artificial intelligence algorithm.

2. The method of claim 1, wherein the acquired biological sensor data includes one or more of auscultation sound data, electrocardiogram (ECG) data, photoplethysmogram (PPG) data, blood pressure data, otoscope data, temperature data, and weight data; and wherein the one or more medical devices and the transmitting device are wirelessly coupled.

3. The method of claim 1, further comprising:
acquiring, at the transmitting device, one or more patient audio data via a microphone and patient video data via a camera, the microphone and the camera communicatively coupled to the transmitting device;
transmitting, in real-time or near real-time, the one or more patient audio data and the patient video data in parallel with the acquired biological sensor data.

4. The method of claim 1, wherein rendering at the receiving device includes displaying, at a display interface of the receiving device, one or more of a result of processing the acquired biological sensor data using the artificial intelligence algorithm, the result indicating a health condition of the patient; one or more biological waveforms based on the acquired biological sensor data; and patient video while outputting audio through an audio output interface of the receiving device, the audio including the result of processing the acquired biological sensor data, one or more heart sounds based on the acquired biological sensor data and patient audio; and wherein the one or more biological waveforms, the patient video, the one or more heart sounds, and the patient audio are rendered in a time synchronized manner.

5. The method of claim 1, further comprising rendering, in real-time or near real-time the acquired biological sensor data at the transmitting device.

6. The method of claim 1, wherein transmitting in real-time or near real-time to the receiving device includes transmitting the acquired biological sensor data to the receiving device via a central server system.

7. The method of claim 1, wherein transmitting in real-time or near real-time to the receiving device includes transmitting the acquired biological sensor data to the receiving device via a peer-to-peer connection.

8. The method of claim 1, wherein the one or more signals include a power on or a power off request for the requested medical device of the one or more medical devices, and the one or more corresponding actions include turning the requested medical device on or off.

9. The method of claim 1, wherein the one or more signals include a recording request, and the one or more corresponding actions include generating a recording of the acquired biological sensor data at the transmitting device or a computing device communicatively coupled to the transmitting device; and storing the recording at the computing device.

10. The method of claim 1, wherein processing the acquired biological sensor data using the artificial intelligence algorithm is performed in response to an analysis request from the receiving device; and wherein processing the acquired biological sensor data using the artificial intelligence algorithm includes transmitting the acquired biological sensor data or a recording of the acquired biological sensor data to a computing device; analyzing, at the computing device, the transmitted biological sensor data or the recording utilizing the artificial intelligence algorithm; and providing a result of the analysis via one or more of the transmitting device and the receiving device.

11. The method of claim 1, wherein processing the acquired biological sensor data using the artificial intelligence algorithm is performed in response to a signal quality of the acquired biological sensor data greater than a threshold.

12. A method for live streaming from a monitoring device, comprising:

acquiring biological sensor data of a patient via a plurality of sensors of the monitoring device;
transmitting, in real-time, the biological sensor data to a transmitting device;
transmitting, in real-time, a data stream including the biological sensor data from the transmitting device to a receiving device;
initiating, via a computing device, an authenticated session for a user via an application executed at the receiving device to access the data stream;
during the authenticated session,
responsive to receiving an analysis request from the receiving device,
performing, at the computing device, a patient condition analysis using an artificial intelligence based algorithm.

13. The method of claim 12, wherein the computing device is a part of a client-server network; and wherein transmitting the data stream to the receiving device includes transmitting the acquired biological sensor data to the receiving device via the computing device.

14. The method of claim 12, wherein transmitting the data stream to the receiving device includes transmitting the acquired biological sensor data to the receiving device via a peer-to-peer connection.

15. The method of claim 12, wherein, the biological sensor data includes one or more of auscultation sound data, electrocardiogram (ECG) data, photoplethysmogram (PPG) data, blood pressure data, otoscope data, temperature data, and weight data.

16. The method of claim 12, further comprising:
at the transmitting device, rendering the biological sensor data, in real-time, via one or more of a sound rendering device coupled to the transmitting device and a display interface of the transmitting device; and
at the receiving device, during the authenticated session, rendering the biological sensor data, in real-time, via one or more of a second sound rendering device coupled to the receiving device and a display interface of the receiving device.

17. The method of claim 12, further comprising:
during the authenticated session, responsive to receiving a recording request from one or more of the computing device and receiving device, initiating a recording of the data stream.

18. The method of claim 12, wherein a result of the patient condition analysis is rendered at one or more of the transmitting device and the receiving device while rendering the biological sensor data.

19. A medical monitoring system, comprising:
one or more monitoring devices, each including one or more sensors for obtaining biological data of a patient;
a transmitting device wirelessly coupled to the one or more monitoring devices; and
a computing device implemented by one or more processors, the one or more processors communicatively coupled to the transmitting device and a receiving device, and configured with instructions in non-transitory memory that when executed cause the one or more processors to:
receive, in real-time, a data stream including the biological data from the one or more monitoring devices via the transmitting device;
initiate an authenticated session for a user to access the data stream via the receiving device;
during the authenticated session, transmit the biological data, in real-time, to the receiving device;
during a first condition of the authenticated session, when a first message is received from the user via the receiving device, process the data stream in real-time based on the first message; and
during a second condition of the authenticated session, when a second message is received from the transmitting device, process the data stream or a first recording of the data stream received from the transmitting device based on the second message;
wherein the first message received from the receiving device includes a first artificial intelligence (AI) analysis request; wherein the second message from the transmitting device includes a second AI analysis request.

20. The medical monitoring system of claim 19, wherein the computing device is further configured with instructions in non-transitory memory that when executed cause the one or more processors to:
in response to the first AI analysis request, perform a health condition analysis on a portion of the data stream or a second recording of the data stream, the second recording generated at the computing device; and transmit a result of the health condition analysis to the receiving device while transmitting the biological data, in real-time, to one or more of the receiving device and the transmitting device; and
in response to the second AI analysis request, perform a second health condition analysis on another portion of the data stream or the first recording of the data stream received from the transmitting device; and transmit a second result of the second health condition analysis to one or more of the receiving device and the transmitting device.

21. The medical monitoring system of claim 19, wherein the biological data includes one or more of auscultation sound data, electrocardiogram (ECG) data, photoplethysmogram (PPG) data, blood pressure data, otoscope data, temperature data, and weight data; and wherein the computing device is configured with further instructions in non-transitory memory that when executed cause the one or more processors to:
receive, in real-time or near real-time, one or more patient audio data and patient video data, from the transmitting device; and
transmit, in real-time or near real-time, the one or more patient audio data and patient video data in parallel with the biological data, to the receiving device.

22. A method, comprising:
acquiring biological sensor data using one or more medical devices;
responsive to a connection request from a receiving device, establishing a wireless connection between a requested medical device of the one or more medical devices and a transmitting device and;
transmitting, in real-time, the acquired biological sensor data to the transmitting device via the wireless connection established between the requested medical device of the one or more medical devices and the transmitting device;
transmitting, in real-time, a data stream including the acquired biological sensor data from the transmitting device to the receiving device; and
responsive to a signal quality of the acquired biological sensor data greater than a threshold, processing the biological sensor data using an artificial intelligence algorithm and/or saving the biological sensor data as a recording.

23. A method for streaming acquired biological sensor data of a patient from one or more medical devices, comprising:
- transmitting, in real-time or near real-time, the acquired biological sensor data, via a transmitting device wirelessly coupled to the one or more medical devices, to a receiving device;
- rendering, in real-time or near real-time, the transmitted biological sensor data at the receiving device; and
- responsive to one or more signals from the receiving device, performing one or more corresponding actions on the acquired biological sensor data;
- wherein the one or more corresponding actions include processing the acquired biological sensor data using an artificial intelligence algorithm in response to an analysis request from the receiving device, including transmitting the acquired biological sensor data or a recording of the acquired biological sensor data to a computing device; analyzing, at the computing device, the transmitted biological sensor data or the recording utilizing the artificial intelligence algorithm; and providing a result of the analysis via one or more of the transmitting device and the receiving device.

* * * * *